United States Patent [19]

McEvoy et al.

[11] 4,226,775

[45] Oct. 7, 1980

[54] SUBSTITUTED THIO-SUBSTITUTED BENZYL-PROPIONYL-L-PROLINES

[75] Inventors: Francis J. McEvoy, Pearl River; Jay D. Albright, Nanuet, both of N.Y.

[73] Assignee: American Cyanamid Company, Stamford, Conn.

[21] Appl. No.: 44,733

[22] Filed: Jun. 1, 1979

Related U.S. Application Data

[63] Continuation-in-part of Ser. No. 939,564, Sep. 5, 1978, abandoned.

[51] Int. Cl.³ .................. C07D 207/16; A61K 31/40
[52] U.S. Cl. .................. 260/326.33; 260/326.43; 260/326.46; 260/326.47; 424/249; 424/251; 424/274; 544/219; 544/316

[58] Field of Search ............ 260/326.47, 326.46, 260/326.33, 326.43, 326.2; 424/274; 544/219, 316

[56] References Cited

U.S. PATENT DOCUMENTS

| | | | |
|---|---|---|---|
| 4,046,889 | 9/1977 | Ondetti et al. | 424/274 |
| 4,052,511 | 10/1977 | Cushman et al. | 429/274 |
| 4,086,338 | 4/1978 | Cushman et al. | 260/326.4 |
| 4,091,024 | 5/1975 | Ondetti et al. | 429/274 |
| 4,105,776 | 8/1978 | Ondetti et al. | 260/326.25 |

*Primary Examiner*—Mary C. Lee
*Attorney, Agent, or Firm*—Edward A. Conroy, Jr.

[57] ABSTRACT

This disclosure describes novel substituted ω-aroyl(propionyl or butyryl)-L-prolines and the esters and cationic salts thereof which are useful as hypotensive agents in mammals.

26 Claims, No Drawings

SUBSTITUTED THIO-SUBSTITUTED BENZYL-PROPIONYL-L-PROLINES

CROSS REFERENCE TO RELATED APPLICATION

This application is a continuation-in-part of our co-pending application Ser. No. 939,564, filed Sept. 5, 1978, now abandoned.

BRIEF SUMMARY OF THE INVENTION

This invention relates to new organic compounds and, more particularly, is concerned with novel substituted ω-aroyl(propionyl or butyryl)-L-prolines and esters thereof which may be represented by the following general formulae:

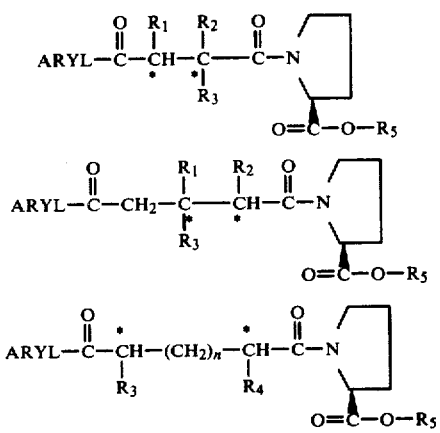

wherein n is zero or one; $R_1$ is hydrogen or alkyl having from 1 to 3 carbon atoms; $R_2$ is hydrogen, phenyl or alkyl having from 1 to 3 carbon atoms; $R_3$ is mercapto, formylthio, benzoylthio, alkanoylthio having from 2 to 4 carbon atoms or moieties of the formulae:

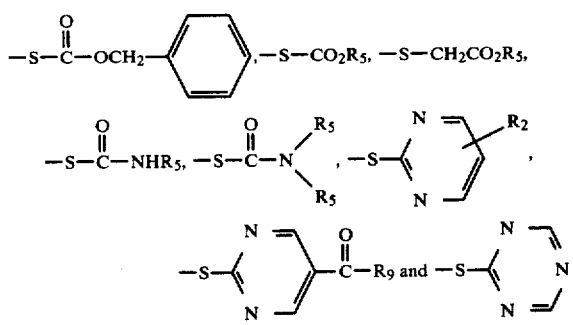

wherein $R_9$ is phenyl or substituted phenyl; $R_4$ is hydrogen, phenyl or alkyl having from 1 to 4 carbon atoms; $R_5$ is hydrogen or alkyl having from 1 to 4 carbon atoms; and ARYL is selected from the group consisting of 1-naphthyl, 2-naphthyl, 4-chloro-1-naphthyl, 4-methoxy-1-naphthyl, 5,6,7,8-tetrahydro-1-naphthyl, 5,6,7,8-tetrahydro-2-naphthyl, 4-biphenylyl, 5-acenaphthyl, 5-indanyl, 4-indanyl and moieties of the formula:

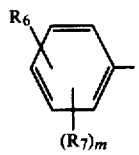

wherein $R_6$ is selected from the group consisting of hydrogen, fluoro, chloro, bromo, trifluoromethyl, cyano, amino, phenoxy, halophenoxy, phenylthio, halophenylthio, p-cyclohexylphenoxy, alkyl having from 1 to 4 carbon atoms, alkoxy having from 1 to 4 carbon atoms, alkylamino having from 1 to 4 carbon atoms, alkanoylamino having from 2 to 4 carbon atoms and alkoxycarbonyl having from 2 to 4 carbon atoms; $R_7$ is selected from the group consisting of chloro, fluoro, bromo, alkyl having from 1 to 4 carbon atoms and alkoxy having from 1 to 4 carbon atoms; and m is zero, one or two. Suitable alkyl and alkoxy groups contemplated by the present invention are, for example, methyl, ethyl, n-propyl, isobutyl, methoxy, ethoxy, isopropoxy, sec-butoxy, etc. while halo is examplified by fluoro, chloro and bromo and alkanoylthio is exemplified by acetylthio, propionylthio, butyrylthio and isobutyrylthio. The novel compounds of the present invention possess asymmetric carbon atoms (which are indicated by asterisks) and thus exist in diastereoisomeric forms.

DETAILED DESCRIPTION OF THE INVENTION

The novel substituted ω-aroyl(propionyl or butyryl)-L-prolines and esters thereof of the present invention are generally obtainable as white to yellow crystalline materials having characteristic melting points and absorption spectra or are obtained as white or yellow glasses with characteristic absorption spectra. They are generally soluble in many organic solvents such as lower alkanols, tetrahydrofuran, dioxane, chloroform, and the like.

Also included within the purview of the present invention are the cationic salts of the compounds of the above general formulae wherein $R_5$ is hydrogen. The useful pharmaceutically acceptable salts of the compounds wherein $R_5$ is hydrogen are those with pharmacologically acceptable metal cations, ammonium, amine cations, or quaternary ammonium cations. Preferred metal cations are those derived from the alkali metals, e.g. lithium, sodium and potassium, and from the alkaline earth metals, e.g. magnesium and calcium, although cationic forms of other metals, e.g. aluminum, copper, iron and in particular zinc, are within the scope of the invention. Pharmacologically acceptable amine cations are those derived from primary, secondary or tertiary amines such as mono-, di- or trimethylamine, ethylamine, dibutylamine, triisopropylamine, N-methylhexylamine, decylamine, allylamine, cyclopentylamine, dicyclohexylamine, mono- or dibenzylamine, α- or β-phenylethylamine, ethylenediamine, and arylaliphatic amines containing up to and including 18 carbon atoms, as well as heterocyclic amines, e.g. piperidine, morpholine, pyrrolidine, piperazine and lower alkyl derivative thereof, e.g. 1-methylpiperidine, 4-ethylmorpholine, 1-isopropylpyrrolidine, 1,4-dimethylpiperazine, and the like, as well as amines containing water-solubilizing or hydrophilic groups, e.g. mono-, di-, or triethanolamine, N-butylethanolamine, 2-amino-1-butanol, 2-amino-2-ethyl-1,3-propanediol, tris(hydroxymethyl)aminomethane, N-phenylethanolamine, galactamine, N-methylglucosamine, ephedrine, phenylephrine, epinephrine, procaine, and the like. Examples of suitable pharmacologically acceptable quaternary ammonium cations are tetramethylammonium, tetraethylammonium, benzyltrimethylammonium, phenyltriethylammonium, and the like.

Angiotensin II is a powerful vasoconstrictor agent that has been implicated as the main causative agent in the etiology of renovascular hypertension. Angiotensin II is formed from angiotensin I by the action of angiotensin converting enzyme. Angiotensin I is a biologically inert decapeptide cleaved from the blood protein angiotensinogen by the action of the enzyme renin [Oparil et al. New England J. of Med., 291, 389–457 (1974)]. Angiotensinogen and renin are also biologically inert. Angiotensinogen converting enzyme is also responsible for the inactivation of bradykinin, a vasodilator agent that has been implicated in the regulation of renal function [Erdos, Circulation Research 36, 247 (1975)]. Agents that inhibit angiotensin converting enzyme can therefore counteract the pressor effect of angiotensin I since this is due only to its conversion to angiotensin II. These agents can be used therapeutically in the treatment of forms of renovascular and malignant hypertension as well as other forms of angiotensin dependent hypertension [Gavras et al., New England J. of Med. 291, 817 (1974)].

The novel compounds of this invention inhibit angiotensin converting enzyme and thus inhibit the conversion of angiotensin I to angiotensin II and are therefore useful in reducing hypertension, especially angiotensin related hypertension in various mammalian species. The activity of the novel compounds of this invention as hypotensive agents was established in two systems which measure their ability as angiotensin converting enzyme inhibitors; namely, a spectrophotometric assay of the compounds in vitro and by the measurement of the blood pressure lowering effect of the compounds in the aorta-coarcted renal hypertensive rats.

Spectrophotometric Assay for Angiotensin Converting Enzyme Inhibitors

The in vitro activity for inhibition of the angiotensin converting enzyme (ACE) was measured by the method of Cushman, D. W. and Cheung, H. S., Biochem. Pharmacol. 20, 1637–1648 (1971), using benzoylglycyl-histidyl-leucine as the substrate. The reaction mixture consisted of 50 ml. of potassium phosphate (500 mM., pH 10.2), 30 ml. of sodium chloride (2500 mM.), 25 ml. of substrate (50 mM), 30 to 50 ml. of the crude extract of ACE, 10 ml. of test compound (2.5 mM) or vehicle and a suitable amount of distilled water to give a total volume of 250 ml. This reaction mixture was incubated for 30 minutes at 37° C. and the reaction was then terminated by the addition of 250 ml. of 1 N hydrochloric acid. The hippuric acid was then extracted with 1.5 ml. of ethyl acetate by vortex mixing for 15 seconds. After centrifugation, 1 ml. of the ethyl acetate layer was pipetted into a new tube and evaporated to dryness. The extracted hippuric acid was then dissolved in 1 ml. of water and the amount of this acid was then measured by its absorbance at 228 nm. The ACE was extracted from rabbit lung acetane powder (Pel-Freez, Biol. Inc.) by blending 5 g. of the powder in 50 ml. of phosphate buffer (50 mM, pH 8.3) and then centrifuging at 40,000 g for 30 minutes. The supernatant was then kept at 5° C. and used as the enzyme source. The activity of the ACE inhibitor was calculated as the percent inhibition of ACE activity compared to the control value of that particular assay. A full dose-response inhibitory curve is then performed to determine the $IC_{50}$ value which may be defined as the molar concentration of a compound that will inhibit the ACE activity by 50%. Representative compounds of the present invention and their corresponding $IC_{50}$ values as determined by the above procedure are set forth in Table I below.

TABLE I

Angiotensin Converting Enzyme Inhibitors

| Compound | $IC_{50}$ $(10^{-7}M)$ |
|---|---|
| 1-(2-Acetylthio-3-benzoylpropionyl)-L-proline | 42.3 |
| 1-(3-Acetylthio-3-benzoyl-2-methylpropionyl 1.47 proline | |
| 1-(3-Acetylthio-3-benzoylpropionyl)-L-proline | 4.55 |
| 1-(3-Benzoylthio-3-benzoylpropionyl)-L-proline | 5.13 |
| 1-[3-Acetylthio-3-(4-fluorobenzoyl)propionyl]-L-proline | 4.73 |
| 1-[3-Benzoylthio-3-(4-fluorobenzoyl)propionyl]-L-proline | 3.53 |
| 1-[3-(4-Bromobenzoyl)-3-thiopropionyl]-L-proline | 3.52 |
| 1-[3-Acetylthio-3-(4-bromobenzoyl)propionyl]-L-proline | 1.31 |
| 1-[3-(4-Bromobenzoyl)-3-benzoylthiopropionyl]-L-proline | 1.15 |
| 1-[3-Acetylthio-3-(4-tert-butylbenzoyl)propionyl]-L-proline | 1.83 |
| 1-[9-Acetylthio-3-(3-trifluoromethylbenzoyl)-propionyl]-L-proline | 10.7 |
| 1-[9-Acetylthio-3-(3-fluoro-4-methoxybenzoyl)-propionyl]-L-proline | 6.0 |
| 1-[3-Acetylthio-3-(3-fluorobenzoyl)-2-methylpropionyl]-L-proline | 0.617 |
| 1-[9-Acetylthio-3-(4-biphenylylcarbonyl)propionyl]-L-proline | 0.86 |
| 1-{3-Acetylthio-3-[4-(4-chlorophenoxy)benzoyl]-propionyl}-L-proline | 3.58 |
| 1-[3-Acetylthio-3-(4-chlorobenzoyl)-2-methyl-propionyl-L-proline | 3.35 |
| 1-[3-Acetylthio-3-(3-fluorobenzoyl)propionyl]-L-proline | 0.316 |
| 1-[3-Acetylthio-3-(4-chlorobenzoyl)propionyl]-L-proline | 0.826 |
| 1-[3-Benzoylthio-3-(3-fluorobenzoyl)propionyl]-L-proline | 17.6 |
| [S-(R*,S*)]-1-[3-(Acetylthio)-3-(3-fluorobenzoyl)-2-methylpropionyl]-L-proline | 0.37 |
| [S-(R*,R*)]-1-[3-(Acetylthio)-3-(3-fluorobenzoyl)-2-methylpropionyl]-L-proline | 2.33 |
| [R-(R*,R*)]-1-[3-Acetylthio)-3-(3-fluorobenzoyl)-2-methylpropionyl]-L-proline | 160 |
| [R-(R*,S*)]-1-[3-Acetylthio)-3-(3-fluorobenzoyl)-2-methylpropionyl]-L-proline | 2800 |
| 1-[3-Acetylthio-3-(2-naphthoyl)-propionyl]-L-proline | 1.3 |
| 1-[3-Benzoyl-2-(carboxymethylthio)propionyl]-L-proline | 316 |
| 1-[3-(5-Benzoyl-2-pyrimidinylthio)-3-p-chlorobenzoylpropionyl]-L-proline | 27.8 |
| 1-[3-(Acetylthio)-3-(5-indanylcarbonyl)propionyl]-L-proline | 2.18 |
| [S-(R*,S*)]-1-[3-(Acetylthio)-3-(4-bromobenzoyl)-2-methylpropionyl]-L-proline | 0.985 |
| [S-(R*,R*)]3-(Acetylthio)-3-(4-bromobenzoyl)-2-methylpropionyl]-L-proline | 1.33 |
| 1-[3-(4-Chlorobenzyl)-3-[5-(2-theonyl)-2-pyrimidinylthio)propionyl]-L-proline | 51.3 |
| [S-(R*,S*)]-1-[3-(Acetylthio)-3-benzoyl-2-methylpropionyl]-L-proline | 0.515 |
| [S-(R*,R*)]-1-[3-(Acetylthio)-3-benzoyl-2-methylpropionyl]-L-proline | 0.78 |

Measurement of Arterial Blood Pressure in
Aorta-Coarcted Renal Hypertensive Rats Male, Sprague-Dawley normotensive rats, weighing 300–325 g. (Charles River Breeding Lab. Inc., Wilmington, Mass.) were maintained on Purina Laboratory Chow and tap water ad libitum for 1–7 days before use. Hypertension was induced by complete ligation of the aorta between the origin of the renal arteries, according to the method of Rojo-Ortega, J. M. and Genest, J., A Method for Production of Experimental Hypertension in Rats, in Can. J. Physiol. Pharmacol. 46, 883–885 (1968), with modifications of the surgical procedures. Thus, rats were anesthetized with methohexitol sodium at 66 mg./kg. of body weight, intraperitoneally and were laid on their right side. An incision was made just below the rib cage on their left side. With a cotton-tip swab, the fat was gently pushed back to expose the left kidney. The kidney was held gently between the thumb and the forefinger outside of the body cavity. The aorta was completely ligated between the origin of the renal arteries with a No.-000 silk suture. Care was taken to avoid the occlusion of the right renal artery. The wound was then closed in two layers using a 4-0 polyglycolic acid suture on the muscle and wound clips on the skin. The wound is then sprayed with No. 3 thimerosal aerosol. Following this surgery, the rats were returned to their cages and provided with Purina Laboratory Chow and water ad libitum. Six days after the surgery, the conscious rats were restrained on rat boards with elastic tape. The neck area was locally anesthetized by subcutaneous infiltration of 2% lidocaine. After the trachea was cannulated and the rat respired spontaneously, the carotid artery was isolated and cannulated with a nylon catheter (inside diameter 0.015", outside diameter 0.030") which was connected to a Statham P23Gb pressure transducer—Gold Brush recorder (Model 2400) for monitoring blood pressure. The test compounds were dissolved in a small amount of ethanol and then diluted to the desired concentration with saline. Both of the solution of the test compound and the vehicle alone were administered orally and run parallel in each experiment. Representative compounds of the present invention were considered active when tested by this procedure.

The novel compounds of the present invention have thus been found to be highly useful for lowering elevated blood pressure in mammals when administered in amounts ranging from about 1 mg. to about 1000 mg. per kilogram of body weight per day. A preferred dosage regimen for optimum results would be from about 10 mg. to about 300 mg. per kilogram of body weight per day. The dosage regimen may be adjusted to provide the optimum therapeutic response. For example, several divided doses may be administered daily or the dose may be proportionally reduced as indicated by the exigencies of the therapeutic situation. The active compounds are preferrably administered orally but may be administered in any convenient manner such as by the intravenous, intramuscular or subcutaneous routes.

Compositions according to the present invention having the desired clarity, stability and adaptability for parenteral use are obtained by dissolving or suspending the active compound in a vehicle consisting of a polyhydric aliphatic alcohol or mixtures thereof. Especially satisfactory are glycerin, propylene glycol and polyethylene glycols. The polyethylene glycols consist of a mixture of non-volatile, normally liquid polyethylene glycols which are soluble in both water and organic liquids and which have molecular weights of from about 200 to 1500. Although the amount of active compound dissolved or suspended in the above vehicle may vary the amount of active substance in the composition is such that dosage in the range of about 10 to 500 mg. of compound is obtained. Although various mixtures of the aforementioned non-volatile polyethylene glycols may be employed, it is preferred to use a mixture having an average molecular weight of from about 200 to about 400.

In addition to the active compound, the parenteral solutions or suspensions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens and thimerosal. As a practical matter, it is also convenient to employ antioxidants, such as, for example, sodium bisulfite, sodium metabisulfite and sodium formaldehyde sulfoxylate. Generally, from about 0.05 to about 0.2% concentrations of antioxidant are employed.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose or lactose may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or suspension may contain the active compound, sucrose as a sweetening agent, methyl and propyl parabens as preservatives, a dye and flavoring such as cherry or orange flavor. Of course, any material used in preparing any dosage unit form should be pharmaceutically pure and substantially non-toxic in the amounts employed.

The novel compounds of formula (III) of the present invention may be prepared in accordance with the following reaction scheme:

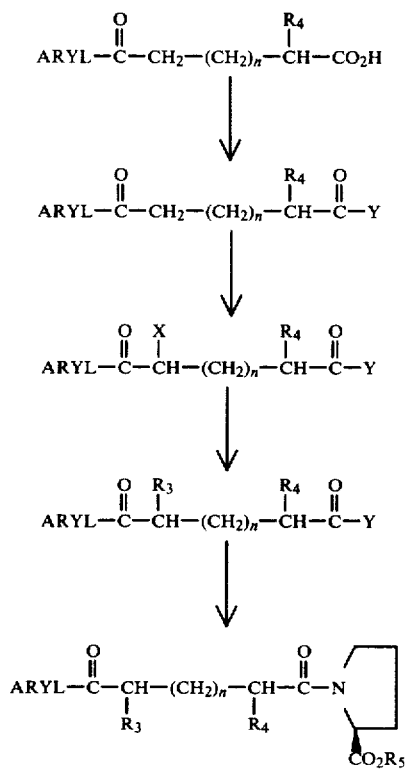

wherein n, $R_3$, $R_4$, $R_5$ and ARYL are as hereinbefore defined; X is chloro, bromo, iodo, —S-R or —$SO_2R$; wherein R is alkyl having 1 to 4 carbon atoms, phenyl, p-tolyl, benzyl, p-methoxybenzyl and the like; and Y is the carbonyl activating residue of a peptide coupling reagent or a group of the formulae:

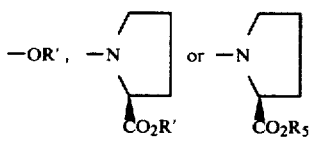

wherein R' is hydrogen, alkyl having 1 to 4 carbon atoms, phenyl, p-tolyl, p-methoxybenzyl, 2,4,6-trimethylbenzyl, trimethylsilyl, 2-trimethylsilylethyl and the like or a suitable carbonyl protecting group; and $R_5$ is as hereinbefore defined.

In accordance with the above reaction scheme, the carboxyl group of an appropriately substituted ω-aroylalkanoic acid (IV) is converted to a carbonyl activated derivative (V) or in accordance with the reaction scheme, derivatives (VI) (Y=OH) and (VII) (Y=OH) are converted to carbonyl activated derivatives. The carbonyl activated derivatives of (V), (VI) and (VII) are prepared by reaction of the free acids under standard reaction conditions for activating the carboxyl groups of N-protected aminoacids. For example, mixed anhydrides are prepared in situ by treatment of the free acids with bases such as trialkylamines (triethylamine and the like), N-methylmorpholine, pyridine, N-methylpiperidine and the like to give the amine salts which are reacted with lower alkyl chloroformates such as ethyl chloroformate, t-butyl chloroformate, isobutyl chloroformate, benzyl chloroformate, trityl chloroformate and the like. Alternatively, the free acids are reacted with N,N'-carbonyldiimidazole or related peptide coupling reagents such as N,N'-carbonyl-1,2,4-triazole to form activated carbonyl derivatives. Derivatives where Y is O-hydroxysuccinimide or O-hydroxyphthalimide are prepared by reaction of the free acids with N-hydroxysuccinimide or N-hydroxyphthalimide in the presence of a carbodiimide such as N,N-dicyclohexylcarbodiimide. Derivatives wherein Y is a residue of a peptide coupling reagent or an activated ester are reacted with L-proline or L-proline derivatives under conventional coupling conditions.

The amides are obtained by reacting an acid halide of (IV) or preferably a carbonyl activated derivative (V) with L-proline or an ester of L-proline such as an alkyl ($C_1$-$C_4$) ester, benzyl ester, 2,4,6-trimethylbenzyl ester and other L-proline derivatives with a protected acid function which is removed in a later step. The reaction conditions for the formation of the carboxyl activated derivatives and conditions for coupling to L-proline or L-proline derivatives, such as time, temperature, solvents, etc. are well known in the art. In general the reactions are carried out at 0° C. to 50° C. in solvents such as tetrahydrofuran, dioxane, N,N-dimethylformamide, dimethylsulfoxide, toluene and the like for 1 to 24 hours.

Further elucidation of the meaning of the terms employed herein is afforded by the following table wherein typical peptide coupling reagents are listed in the left column and the corresponding carbonyl activating residues are listed in the right column:

| Reagent | —Y |
|---|---|
| N-hydroxyphthalimide | (phthalimide-O-N structure) |
| dicyclohexylcarbodiimide | —O—C(=N-cyclohexyl)—NH-cyclohexyl |
| N,N'-carbonyldiimidazole | —N(imidazole) |
| benzyl chloroformate | —O—C(=O)—$CH_2$—phenyl |
| N-hydroxysuccinimide | —O—N(succinimide) |
| activated ester | —S—Aryl |
| mixed anhydride | —O—C(=O)—$C(CH_3)_3$ |
| | —O—C(=O)—O—Alkyl |
| | —$SO_2$—Aryl |

Numerous other peptide coupling reagents are available and well known to the art such as unsaturated ethers, α-chlorovinyl ethyl ether, ethoxyacetylene, ketenimines and ketenes, ynamines, acyloxyphosphonium ions, EEDQ, silicon tetrachloride, 1,2-oxazolium salts, and the like. These all provde a carbonyl activating residue (—Y) and may be readily used for the conversion of (VI) to (V) when Y is to be a "carbonyl activating residue of a peptide coupling reagent". The reaction conditions for such conversions are well known in the art and may be readily found in such literature references as SYNTHESIS, Sept. 1972, pages 453–463 by Klausner & Bodansky.

The conversion of the intermediates (V) to the corresponding 3-(X-substituted)propionic or 4-(X-substituted)-butyric acid derivatives (VI) wherein X consists of the hereinabove defined leaving groups is readily achieved by conventional methods well known in the art. For example, the chloro, bromo and iodo derivatives may be prepared by treating a compound of formula (V) with a halogenating agent such as chlorine, bromine, N-iodosuccinimide, and the like in a solvent such as chloroform, carbon tetrachloride, acetic acid or dioxane at 25°–75° C. for 12–24 hours. Those compounds wherein X is —S—R may be obtained from the halo derivatives by treatment with an alkali metal mercaptide under standard conditions. The corresponding derivatives wherein $X = SO_2R$ may be obtained by oxidation of the corresponding mercapto derivatives with oxidizing agents such as meta-periodic acid and the like in an inert solvent at 10°–100° C. for 1–24 hours. As desired, the ω-aroylalkanoic acids (IV) may be coupled to an L-proline derivative

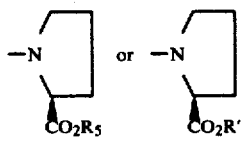

to give intermediates (V) which are then converted to products (III) through intermediates (VI) and (VII). Alternatively, intermediates (V) wherein Y is a carboxyl protecting group may be converted to intermediates (VI) or (VII) at which point the protecting group may be removed and the intermediates (VI) or (VII) (Y=OH) coupled to L-proline or L-proline derivatives.

The ω-aroylalkanoic acids (IV) wherein $R_4$ is other than hydrogen have one asymmetric carbon atom and the D and L isomers may be prepared by resolution of the racemic mixture. Activation of the carboxyl group of the resolved isomers then gives compounds of structure (V) wherein the carbon atom bearing the $R_4$ group has either the D or the L configuration. Conversion of the resolved compounds of structure (V) to the reactive intermediates (VI) gives compounds which are diastereoisomers. Each diastereoisomer may then be converted to compounds of structure (VII) as shown in the reaction scheme. Alternatively, racemic compounds of structure (IV) wherein $R_4$ is lower alkyl may be coupled to L-proline or L-proline derivatives to give compounds of structure (V) which exist as diastereoisomeric forms and may be separated by conventional means. For example, the diastereoisomeric forms of 1-(3-benzoyl-2-methylpropionyl)-L-proline may be separated by preferential crystallization of one diastereoisomer and isolation of the other diastereoisomer from the mother liquors. In this manner diastereoisomeric forms of structural type (VI) may be prepared and converted to the compounds of structure (III) which are inhibitors of the angiotension converting enzyme. The reactive intermediates (VI) are reacted with the anion of a thioacid of formula

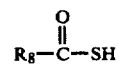

wherein $R_8$ is phenyl, alkyl having up to 3 carbon atoms or other thiolating reagents (H—$R_3$). Suitable anions of thioacids and thiolating reagents useful in the displacement reaction are those from alkali metals (K+, Na+), alkaline earth metals such as calcium and magnesium, and organic bases such as ammonia, trialkylamines, and the like. Removal of the acyl group by reaction with hydroxylamine, ammonium hydroxide or dilute inorganic bases gives the compounds of structure (III) wherein $R_3$ is mercapto. Under appropriate conditions intermediates (VI) and (VII) wherein X is —S—R and Y is

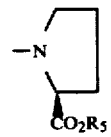

may be converted directly to products (III) wherein $R_3$ is —SH by removal of a thio protecting group. For example, derivatives wherein R is a thio protecting group such as t-butyl, p-methoxybenzyl, $PhCH_2O_2CS$— and the like may be deblocked under acidic conditions [HBr-HOAc, $CF_3CO_2H$, $(CF_3CO_2)_2Hg$ and the like] known to the art.

Derivatives (VII) wherein Y is

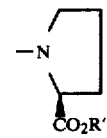

and $R_3$ is as previously defined and R' is a carboxyl protecting group may be converted to products (III) ($R_5$=H) by removal of the carboxyl protecting group under conventional conditions. In general carboxyl protecting groups which are removed under acidic conditions are preferred. For example, t-butylesters are cleaved by treatment with trifluoroacetic acid or aqueous trifluoroacetic acid at 0° C. to 50° C. for 1 to 24 hours. Trimethylsilyl and 2-trimethylsilylethyl are removed under conventional conditions known to the art. The reactions illustrated in the reaction scheme may be carried out with esters ($R_5$=lower alkyl) to give the products (III) wherein $R_5$ is lower alkyl. In the products (III) (wherein $R_5$ is tert-butyl) the ester group may be removed in the presence of trifluoroacetic acid to give the free acid derivatives of (III).

The novel compounds of formula (I) of the present invention may be prepared in accordance with the following reaction scheme:

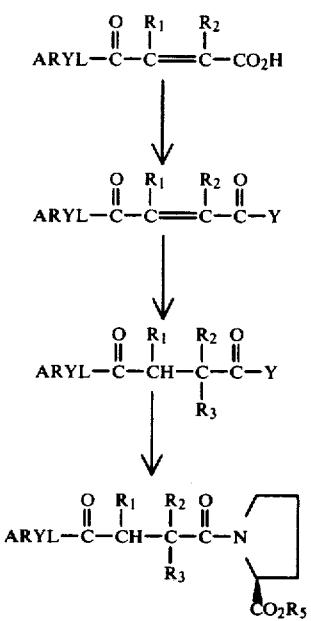

and the novel compounds of formula (II) of the present invention may be prepared in accordance with the following reaction scheme:

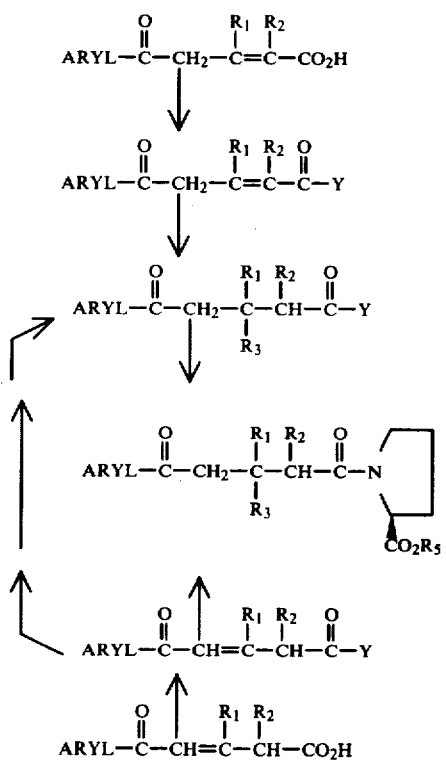

wherein $R_1$, $R_2$, $R_3$, $R_5$, ARYL and Y are as hereinbefore defined. In accordance with the above reaction schemes, an appropriately substituted ω-aroylacrylic acid (VIII), ω-aroylcrotonic acid (XI) or 3-aroyl-3-butenoic acid (XIV) is converted to a carbonyl activated derivative (IX), (XII) or (XV). The reaction conditions for the formation of such carbonyl activated derivatives such as time, temperature, solvents, etc. are well known in the art and are hereinbefore discussed for the conversion of (IV) to products (III). The carboxyl activated derivatives (IX), (XII) and (XV) are prepared by treatment of the free acids (VIII), (XI) or (XIV) with peptide coupling reagents as hereinbefore discussed. (See table of carbonyl activating residues).

Derivatives (IX), (XII) or (XV) wherein Y is a residue of a peptide coupling reagent or an activated ester are reacted with L-proline or an L-proline derivative of the formulae:

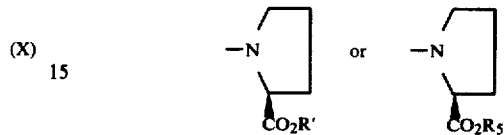

wherein R' and $R_5$ are as previously defined to give intermediates containing a double bond in conjugation with a carbonyl group. The intermediates (IX), (XII) and (XV) are reacted with a thiolating reagent which gives the products (I) or (II) directly or intermediates (X) or (XIII) convertible into products (I) or (II). The position of the double bond determines the direction of the 1,4-addition of the thiolating reagent as shown in the reaction scheme. Thiolating reagents add 1,4 to the ketone carbonyl of intermediates (VIII), (IX), (XIV) and (XV) while addition occurs 1,4 to the carboxyl group in derivatives (XI) and (XII). Suitable thiolating reagents are $H_2S$, $H-S-C(CH_3)_3$, and $H-R_3$ wherein $R_3$ is as hereinbefore defined. Preferred reagents are hydrogen sulfide or a thiolating agent of the formula:

wherein $R_8$ is hydrogen, phenyl or alkyl having up to 3 carbon atoms.

The preferred conditions for the addition of a thiolating reagent are reaction in inert solvents such as chloroform, dichloromethane, carbon tetrachloride, dimethylformamide, tetrahydrofuran, dioxane, acetonitrile, toluene, lower alkanols and the like at 0° C. to 100° C. for one to 24 hours. Conversion of compounds (X) and (XIII) wherein Y is a group of the formula:

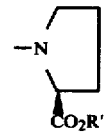

and R' is a carboxyl protecting group as previously defined is carried out by removal of the protecting group to give products (I) and (II) wherein $R_5=H$. Carboxyl protecting groups which are removed under acidic conditions are preferred. The reactions illustrated in the reaction scheme may be carried out with esters of L-proline ($R_5$=lower alkyl) to give the products (I) and (II) wherein $R_5$ is lower alkyl. In the products wherein $R_5$ is tert-butyl the ester group may be removed in the presence of trifluoroacetic acid or aqueous trifluoroacetic acid to give the free acid derivatives of (I) and (II). Conversion of compounds of formulae (X) and (XIII) to final products (I) and (II) is achieved as set forth hereinbefore for the conversion of (VII) to (III). Derivatives which contain a thio protecting group may be converted to products (I) or (II) wherein $R_3$ is —SH by removing the protecting group under conventional conditions.

The invention will be described in greater detail in conjunction with the following specific examples.

EXAMPLE 1

2-Methyl-3-(m-trifluoromethylbenzoyl)propionic acid

To a solution of 60.0 g. of α-(m-trifluoromethylphenyl)-4-morpholineacetonitrile in 200 ml. of tetrahydrofuran is added 10 ml. of 30% potassium hydroxide in ethanol, followed by the rapid addition of 22.0 ml. of methacrylonitrile (exothermic). The mixture is stirred at room temperature overnight and the solvent is removed. To the residue is added 200 ml. of acetic acid and 20 ml. of water and this mixture is refluxed for 2 hours. The solvent is removed in vacuo and 200 ml. of 6 N hydrochloric acid is added to the residue. This mixture is refluxed for 18 hours, cooled and extracted with dichloromethane. The dichloromethane extract is passed through a column of hydrous magnesium silicate. The eluate is concentrated in vacuo and crystallized from dichloromethane-hexane giving 55 g. of off-white crystals. These crystals are dissolved in dichloromethane and extracted with saturated sodium bicarbonate solution. The aqueous extract is acidified with hydrochloric acid and extracted with dichloromethane. This organic extract is passed through hydrous magnesium silicate and the eluate is concentrated. The residue is crystallized from dichloromethane-hexane, giving 39 g. of the desired product as off-white crystals m.p. 90°–91° C.

EXAMPLE 2

3-(m-Fluorobenzoyl)-2-methylpropionic acid

A solution of 48.0 g. of α-(m-fluorophenyl)-4-morpholineacetonitrile in 200 ml. of tetrahydrofuran is reacted as described in Example 1, giving 34 g. of the desired product as off-white crystals, m.p. 192°–194° C.

EXAMPLE 3

1-(3-Benzoylpropionyl)-L-proline methyl ester

A mixture of 3.56 g. of 3-benzoylpropionic acid and 3.24 g. of N,N-carbonyldiimidazole in 30 ml. of tetrahydrofuran is stirred at room temperature for 30 minutes. A 3.32 g. portion of L-proline methyl ester hydrochloride is added and the mixture is stirred at room temperature for 2.5 days. The solvent is removed in vacuo. Water and dichloromethane are added to the residue and the organic layer is separated, washed with water, then with 0.1 N hydrochloric acid and dried over magnesium sulfate. The solvent is removed in vacuo, giving 5.0 g. of the desired product as off-white crystals, m.p. 66°–70° C.

EXAMPLE 4

3-Bromo-3-(p-fluorobenzoyl)propionic acid

To a solution of 19.62 g. of 3-(p-fluorobenzoyl)propionic acid in 100 ml. of acetic acid, is added 16 g. of bromine. The mixture is stirred for 18 hours and then the solvent is removed. Ice and water are added to the residue and the mixture is filtered. The solid is washed with water and then dissolved in 80 ml. of acetone. The solution is diluted with 400 ml. of hexane and allowed to evaporate, at room temperature, to a volume of 125 ml. A 100 ml. portion of hexane is added and the mixture is filtered, giving 24.6 g. of the desired product as tan crystals, m.p. 131°–135° C.

EXAMPLE 5

2-Methyl-3-(benzoyl)propionic acid

To a solution of 40.4 g. of α-(phenyl)-4-morpholineacetonitrile in 400 ml. of tetrahydrofuran is added 10 ml. of 30% potassium hydroxide in ethanol. A 21 ml. portion of methacrylonitrile is added dropwise (exothermic) and the mixture is stirred for 18 hours. The solvent is removed in vacuo, the residue is dissolved in ether-acetone and filtered. The filtrate is concentrated and the residue is triturated with hexane, chilled and filtered giving 51.1 g. of 4methyl-2-morpholine-2-(phenyl)glutaronitrile as white crystals, m.p. 93°–98° C.

A mixture of 5.0 g. of 4-methyl-2-morpholine-2-(phenyl)-glutaronitrile, 26 ml. of acetic acid and 2.9 ml. of water is refluxed for one hour. The solvent is removed in vacuo and the residual gum is partitioned between water and dichloromethane. The dichloromethane is separated, washed with water, dried over magnesium sulfate and the solvent removed, giving 2-methyl-3-(benzoyl)propionitrile as a gum. A 30 ml. portion of concentrated hydrochloric acid is added to this gum, the mixture is refluxed for one hour, cooled, filtered and the solid is washed with water, giving the desired product as white crystals, m.p. 143°–145° C.

EXAMPLE 6

2-Methyl-3-(p-trifluoromethylbenzoyl)propionic acid

To a solution of 54.0 g. of α-(p-trifluoromethylphenyl)-4-morpholineacetonitrile in 400 ml. of tetrahydrofuran is added 10 ml. of 10% potassium hydroxide in ethanol. A 28 ml. portion of methacrylonitrile is added dropwise (exothermic) and the mixture is stirred at room temperature for 18 hours. The solvent is removed. The residual oil is dissolved in ether and the solution is washed with water, sodium chloride solution and dried over magnesium sulfate. The solvent is removed and the residue crystallized from hexane containing a small amount of ether. The gummy yellow solid is dissolved in acetone, heated to boiling and hexane is added until crystals separate. These crystals are recovered by chilling and filtration and recrystallized twice from acetone-hexane giving 16.1 g. of 4-methyl-2-morpholino-2-(p-trifluoromethylphenyl)glutaronitrile as white crystals, m.p. 156°–159° C.

A mixture of 35 g. of 4-methyl-2-morpholino-2-(p-trifluoromethylphenyl)glutaronitrile in 170 ml. of acetic acid and 17.5 ml. of water is refluxed for 2 hours. The solvent is removed and the residue is triturated with hexane-ether, giving an orange solid. This solid is recrystallized from acetone-hexane, giving 17.7 g. of 2methyl-3-(p-trifluoromethylbenzoyl)-propionitrile as yellow crystals, m.p. 94°–96° C.

A mixture of 13.0 g. of 2methyl-3-(p-trifluoromethylbenzoyl)propionitrile in 130 ml. of concentrated hydrochloric acid is refluxed for 5 hours, then chilled and filtered. The solid is washed with water giving 13.7 g. of the desired product as off-white crystals, m.p. 116°–119° C.

EXAMPLE 7

2-Methyl-3-(benzoyl)propionic acid hydroxysuccinimide ester

To a mixture of 12.86 g. of 2-methyl-3-(benzoyl)propionic acid (Example 5) and 7.71 g. of N-hydroxysuccinimide in 70 ml. of dioxane is added a solution of 13.8 g. of dicyclohexylcarbodiimide in 50 ml. of dioxane. The mixture is stirred at room temperature for 18 hours, filtered and the filtrate concentrated in vacuo to an oil. This oil is crystallized with hexane containing a small amount of ether. The solid is recrystallized from dichloromethane, giving 12.0 g. of the desired product as white crystals, m.p. 112°–115° C.

EXAMPLE 8

1-(2-Acetylthio-3-benzoylpropionyl)-L-proline

To a solution of 26.4 g. of benzoylacrylic acid and 17.25 g. of N-hydroxysuccinimide in 165 ml. of dioxane is added a solution of 30.9 g. of dicyclohexylcarbodiimide in 120 ml. of dioxane. The mixture is stirred at room temperature for 18 hours, filtered and the filtrate is concentrated to dryness in vacuo. The residual oil is triturated with hexane giving a waxy solid. This solid is dissolved in 250 ml. of dichloromethane and hexane is added until the solution becomes turbid. Chilling and filtration gives 18.2 g. of the hydroxysuccinimide ester of benzoylacrylic acid as yellow crystals. These crystals are slurried in 240 ml. of ethanol and added to a solution of 7.71 g. of L-proline and 11.26 g. of soduim bicarbonate in 240 ml. of water. The mixture is stirred at room temperature for 18 hours and then concentrated to ½ its volume. The mixture is cooled, acidified with concentrated hydrochloric acid and extracted with dichloromethane. The extract is washed with water and sodium chloride solution and dried over magnesium sulfate. The solvent is removed in vacuo leaving a gum which is triturated with ethyl acetate-hexane-acetic acid (75:25:2) giving 10.1 g. of 1-(3-benzoylacryloyl)-L-proline as off-white crystals, m.p. 122°–124° C.

A mixture of 2.57 g. of 1-(3-benzoylacryloyl)-L-proline, 1.42 ml. of thioacetic acid and 30 ml. of carbon tetrachloride is stirred for one hour and then concentrated in vacuo to an amber gum. This gum is dissolved in dichloromethane and the solvent removed in vacuo several times giving the desired product as an off-white glass.

EXAMPLE 9

1-(3-Benzoyl-2-methylpropionyl)-L-proline

To a solution of 4.8 g. of L-proline and 6.97 g. of sodium bicarbonate in 170 ml. of water is added a slurry of 12.0 g. of 2-methyl-3-(benzoyl)propionic acid hydroxysuccinimide ester (Example 7) in ethanol and the mixture is stirred at room temperature for 18 hours. The volume is reduced 50% in vacuo and while cooling, acidified with hydrochloric acid. The mixture is extracted with dichloromethane. The organic extract is washed with sodium chloride solution, dried over magnesium sulfate and the solvent is removed in vacuo giving a gum. This gum is dissolved in 60 ml. of warm acetic acid, 5 ml. of concentrated hydrochloric acid is added and while cooling water is added until the solution is turbid. Chilling and filtration gives a solid which is recyrstallized from acetone-dichloromethane to give the desired product as white crystals, m.p. 218°–220° C. (designated isomer A).

The mother liquors from which isomer A crystallizes are concentrated to a glass. The glass is purified by chromatography to give a glass (designated isomer B). These two isomers designated A and B are the two diastereoisomers in which the chiral carbon bearing the 2-methyl group is in the R or S configuration.

EXAMPLE 10

3-Acetylthio-3-( B 4-fluorobenzoyl)propionic acid

A mixture of 2.75 g. of 3-bromo-3-(p-fluorobenzoyl)-propionic acid (Example 4), 2.3 g. of potassium thioacetate and 40 ml. of acetonitrile is stirred at room temperature for 6 hours. The mixture is filtered and the filtrate is concentrated in vacuo. The residue is mixed with water and extracted with dichloromethane. The organic extract is washed with water, dried over magnesium sulfate and the solvent removed in vacuo giving the desired product as a gum.

EXAMPLE 11

1-(3-Benzoyl-3-bromo-2-methylpropionyl)-L-proline

To a mixture of 1.25 g. of 1-(3-benzoyl-2-methylpropionyl)-L-proline (isomer A of Example 9) in 30 ml. of acetic acid, is added 0.7 g. of bromine in 10 ml. of acetic acid. The mixture is stirred at room temperature for 18 hours, the solvent is concentrated in vacuo to ½ volume and the mixture is poured into ice and water. This mixture is extracted with dichloromethane. The organic extract is washed with water, then sodium chloride solution, dried over magnesium sulfate and the solvent is removed in vacuo giving a gum. This gum is dissolved in dichloromethane, hexane is added and the solvent is removed at room temperature giving a white glass. This glass is chromatographed on a silica gel column with ethyl acetate-hexane-acetic acid (75:25:2) giving 1.25 g. of the desired product as a white glass (3-bromo derivative of isomer A).

In a similar manner 1-(3-benzoyl-2-methylpropionyl)-L-proline (isomer B of Example 9) is reacted with bromine in acetic acid to give a glass (3-bromo derivative of isomer B).

EXAMPLE 12

1-(3-Acetylthio-3-benzoyl-2-methylpropionyl)-L-proline

To a suspension of 0.47 g of potassium thioacetate in 10 ml. of ethanol is added 1.25 g. of 1-(3-benzoyl-3-bromo-2-methylpropionyl)-L-proline (Example 11, 3-bromo derivative of isomer A). The mixture is stirred for 18 hours, the solvent is removed in vacuo and the residue is partitioned between dichloromethane and water. The organic layer is washed with water, then sodium chloride solution and dried over magnesium sulfate. The solvent is removed in vacuo giving a yellow glass which is dissolved in 10 ml. of ethanol. A 0.47 g. portion of potassium thioacetate is added and the above procedure is repeated giving a yellow glass. This glass is purified by chromatography on a silica gel column with ethyl acetate-hexane-acetic acid (75:25:2) giving 0.28 g. of the desired product as a yellow glass.

In a similar manner 1-(3-benzoyl-3-bromo-2-methylpropionyl)-L-proline (Example 11, 3-bromo derivative of isomer B) is reacted with potassium thioacetate to give a glass.

EXAMPLE 13

3-(p-Chlorobenzoyl)propionic acid hydroxysuccinimide ester

To a mixture of 10.7 g. of 3-(p-chlorobenzoyl)propionic acid and 5.75 g. of N-hydroxysuccinimide in 100 ml. of dioxane is added 10.3 g. of dicyclohexylcarbodiimide. The mixture is stirred at room temperature for 3 hours and then refrigerated for 18 hours. Filtration and evaporation of the filtrate gives a residue which is rubbed with petroleum ether (b.p. 30°-60° C.) giving a gummy tan solid. This solid is dissolved in 50 ml. of dichloromethane. A 50 ml. portion of petroleum ether (b.p. 30°-60° C.) is added producing turbidity. This mixture is cooled and the desired product is recovered by filtration as white crystals, m.p. 121°-123° C.

EXAMPLE 14

3-(p-Fluorobenzoyl)propionic acid hydroxysuccinimide ester

To a solution of 25.0 g. of 3-(p-fluorobenzoyl)propionic acid and 14.7 g. of N-hydroxysuccinimide in 140 ml. of dioxane is added a solution of 26.4 g. of dicyclohexylcarbodiimide in 100 ml. of dioxane. The mixture is stirred at room temperature for 18 hours, filtered and the filtrate is evaporated to dryness in vacuo, leaving a red oil. This oil is rubbed with hexane giving a red solid. This solid is dissolved in 200 ml. of dichloromethane and 200 ml. of hexane is added producing turbidity. The mixture is cooled in an ice bath for 2 hours giving the desired product as white crystals, m.p. 130°-132° C.

EXAMPLE 15

3-Benzoylpropionic acid hydroxysuccinimide ester

To a partial solution of 53.4 g. of 3-benzoylpropionic acid and 34.5 g. of N-hydroxysuccinimide in 325 ml. of dioxane is added a solution of 61.8 g. of dicyclohexylcarbodiimide in 225 ml. of dioxane. The mixture is stirred at room temperature for 18 hours, filtered and the filtrate is evaporated to dryness in vacuo. The residue is triturated with hexane and filtered giving a solid which is dissolved in 700 ml. of dichloromethane and filtered. A 700 ml. portion of hexane is added to the filtrate producing turbidity. Refrigeration produces a solid which is recovered by filtration and washed with 250 ml. of dichloromethane-hexane (1:1) giving the desired product as white crystals, m.p. 130°-132° C.

EXAMPLE 16

1-(3-Benzoylpropionyl)-L-proline

To a solution of 25.5 g. of L-proline and 37.3 g. of sodium bicarbonate in 800 ml. of water is added a slurry of 61.0 g. of 3-benzoylpropionic acid hydroxysuccinimide ester (Example 15) in 800 ml. of ethanol. The mixture is concentrated to ½ volume, cooled and acidified with concentrated hydrochloric acid. The mixture is extracted with dichloromethane and the extract washed with water, saturated sodium chloride and dried over magnesium sulfate. The solvent is removed under vacuum to give an orange gum which is rubbed to a solid with ether containing a little dichloromethane. This solid is recrystallized from 250 ml. of acetone by displacing with hexane. Cooling for 2 hours gives 32.6 g. of the desired product as white crystals, m.p. 95°-97° C.

EXAMPLE 17

1-[3-(4-Fluorobenzoyl)propionyl]-L-proline

To a solution of 10.6 g. of L-proline and 15.5 g. of sodium bicarbonate in 370 ml. of water is added a slurry of 26.9 g. of 3-(p-fluorobenzoyl)propionic acid hydroxysuccinimide ester (Example 14) in 370 ml. of ethanol. The mixture is treated as described in Example 16, giving 13.1 g. of the desired product as white crystals, m.p. 127°-129° C.

EXAMPLE 18

1-[3-(4-Chlorobenzoyl)propionyl]-L-proline

To a solution of 2.30 g. of L-proline and 3.36 g. of sodium bicarbonate in 50 ml. of water is added a partial solution of 5.96 g. of 3-(p-chlorobenzoyl)propionic acid hydroxysuccinimide ester (Example 13) in 60 ml. of ethanol. The procedure of Example 16 is followed giving 3.37 g. of the desired product, m.p. 137°-138° C.

EXAMPLE 19

1-[3-Bromo-3-(4-fluorobenzoyl)propionyl]-L-proline

To a solution of 10.26 g. of 1-[3-(4-fluorobenzoyl)propionyl]-L-proline (Example 17) in 100 ml. of acetic acid is added 3 drops of 30% hydrogen bromide in acetic acid. A solution of 5.6 g. of bromine in 20 ml. of acetic acid is then added dropwise and the mixture is stirred at room temperature overnight. The mixture is evaporated to ⅓ its volume, poured into ice and water and extracted with dichloromethane. The organic extract is washed twice with water and then with saline, dried over magnesium sulfate and evaporated to dryness in vacuo with moderate heat, giving a white glass. This glass is scraped from the flask giving 12.2 g. of white powder. This powder is dissolved in ethyl acetate-hexane-acetic acid (75:25:2), placed on a 1½"×20" silica gel column and eluted with the same solvent system, taking 100 ml. cuts with a 300 ml. fore-cut and a 400 ml. hold back volume. Cuts 2, 5 and 6 are combined and re-columned in the same manner. Cut 2 gives the desired product as 2.0 g. of a white glass.

EXAMPLE 20

1-(3-bromo-3-benzoylpropionyl)-L-proline

To a solution of 8.25 g. of 1-(3-benzoylpropionyl)-L-proline (Example 16) in 80 ml. of acetic acid is added 5 drops of 30% hydrogen bromide in acetic acid followed by 4.80 g. of bromine in 20 ml. of acetic acid. The mixture is stirred at room temperature for 18 hours, evaporated to ⅓ its volume, poured into ice and water and extracted with dichloromethane. The organic extract is washed with water and saline, dried over magnesium sulfate and evaporated to dryness giving the desired product as 10.3 g. of a white glass.

EXAMPLE 21

1-(3-Acetylthio-3-benzoylpropionyl)-L-proline

To a stirred mixture of 1.25 g. of potassium thioacetate in 20 ml. of ethanol is added a solution of 3.54 g. of 1-(3-bromo-3-benzoylpropionyl)-L-proline (Example 20) in 20 ml. of ethanol. The mixture is stirred at room temperature for 2 hours. The mixture is concentrated to dryness under vacuum and the residue partitioned between dichloromethane and water. The dichloromethane layer is washed with saturated sodium chloride solution and dried over magnesium sulfate. The solvent is removed under vacuum to give 2.9 g. of product as a glass. A 2.3 g. sample is chromatographed over silica gel with solvent system, ethyl acetate-hexane-acetic acid (75:25:2) to give 1.07 g. of product as a pale yellow glass.

EXAMPLE 22

1-(3-Benzoylthio-3-benzoylpropionyl)-L-proline

To 440 mg. of a sodium hydride in oil dispersion (washed twice with hexane) is added a solution of 1.60 g. of thiobenzoic acid in 25 ml. of ethanol. The mixture is stirred for 30 minutes and then 3.54 g. of 1-(3-bromo-3-benzoylpropionyl)-L-proline is added and the mixture is stirred at room temperature for 18 hours. The procedure of Example 12 is followed giving the desired product as a glass.

EXAMPLE 23

1-[3-Acetylthio-3-(4-fluorobenzoyl)propionyl]-L-proline

To a solution of 3.7 g. of 1-[3-bromo-3-(4-fluorobenzoyl)propionyl]-L-proline (Example 19) in 37 ml. of ethanol is added 1.37 g. of potassium thioacetate. The procedure of Example 12 is followed giving the desired product as 1.02 g. of a glass.

EXAMPLE 24

1-[3-Benzoylthio-3-(4-fluorobenzoyl)propionyl]-L-proline

To 440 mg. of a sodium hydride in oil dispersion (washed twice with hexane) is added dropwise a solution of 1.60 g. of thiobenzoic acid in 25 ml. of ethanol. The mixture is stirred at room temperature for one hour and 3.7 g. of 1-[3-bromo-3-(4-fluorobenzoyl)propionyl]-L-proline (Example 19) is added. The procedure of Example 12 is followed giving the desired product as 3.81 g. of a white glass.

EXAMPLE 25

1-[3-(4-Bromobenzoyl)propionyl]-L-proline tert-butyl ester

A solution of 1.285 g. of p-bromobenzoylpropionic acid and 0.50 ml. of triethylamine in 25 ml. of tetrahydrofuran is stirred in an ice-salt bath at −8° C. A solution of 0.48 ml. of ethyl chlorocarbonate in 5 ml. of tetrahydrofuran is added dropwise and the mixture is stirred at −5° C. for 30 minutes. A solution of 855 mg. of t-butylproline in 10 ml. of tetrahydrofuran is added dropwise, the solution is stirred in the ice-salt bath for 30 minutes and then allowed to stand at room temperature for 30 minutes. The mixture is poured into ice and water, extracted with dichloromethane and the organic extract is washed with saturated aqueous sodium bicarbonate, water, then 1 N hydrochloric acid, dried over magnesium sulfate and evaporated in vacuo to dryness leaving an oil. This oil is crystallized from hexane containing a small amount of ether giving an off-white solid which is recrystallized from acetone-hexane giving the desired product as 505 mg. of white crystals, m.p. 70°–71° C.

EXAMPLE 26

1-[3-(4-Bromobenzoyl)propionyl]-L-proline methyl ester

A solution of 5.14 g. of p-bromobenzoylpropionic acid and 2.78 ml. of triethylamine in 50 ml. of tetrahydrofuran is stirred and cooled to −15° C. in a methanol-ice-salt bath. A solution 1.9 of ethyl chlorocarbonate in 10 ml. of tetrahydrofuran is added dropwise and the mixture is stirred at −10° C. for 30 minutes.

A solution of 3.32 g. of methylproline hydrochloride in 50 ml. of methylene chloride is treated with 2.78 ml. of triethylamine for 15 minutes and then filtered. The filtrate is then added dropwise to the above solution, maintaining the temperature below −5° C. The mixture is stirred in the bath for 30 minutes and then allowed to come to room temperature over one hour. The mixture is poured into 300 ml. of water and extracted with dichloromethane. The organic extract is washed with saturated aqueous sodium bicarbonate, water, then 1 N hydrochloric acid, dried over magnesium sulfate and evaporated to an oil. This oil is rubbed to a solid with petroleum ether (b.p. 30°–60° C.) and then recrystallized from acetone-hexane giving the desired product as 2.09 g. of white crystals, m.p. 84°–86° C.

EXAMPLE 27

3-(4-Bromobenzoyl)propionic acid hydroxysuccinimide ester

A solution of 41.2 g. of dicyclohexylcarbodiimide in 150 ml. of dioxane is added to a partial solution of 51.4 g. of p-bromobenzoylpropionic acid and 23.0 g. of N-hydroxysuccinimide in 250 ml. of dioxane. The mixture is stirred at room temperature for 18 hours, then stirred in an ice bath, filtered and the filtrate is evaporated in vacuo to a residue. This residue is triturated in hexane and rubbed to a solid. The solid is dissolved in 130 ml. of dichloromethane and 120 ml. of petroleum ether (b.p. 30°–60° C.) is added producing turbidity. Cooling in an ice bath gives the desired product as 31.1 g. of white crystals, m.p. 127°–129° C.

EXAMPLE 28

1[3-(4-Bromobenzoyl)propionyl]-L-proline methyl ester

To a solution of 3.54 g. of 3-(4-bromobenzoyl)propionic acid hydroxysuccinimide ester (Example 27) and 1.66 g. of methylproline hydrochloride in 10 ml. of acetonitrile is added 1.75 ml. of diisopropylethylamine. The mixture is stirred at room temperature for 18 hours and evaporated in vacuo to a residue. This residue is dissolved in dichloromethane, washed with 1 N hydrochloric acid, dried over magnesium sulfate and evaporated in vacuo to a gum. This gum is rubbed to a solid with hexane and then recrystallized from acetone-hexane giving the desired product as 2.01 g. of a white solid, m.p. 78°–82° C.

EXAMPLE 29

1-[3-(4-Bromobenzoyl)propionyl]-L-proline methyl ester

The procedure of Example 28 is repeated, using 21.8 ml. of triethylamine in place of the diisopropylethylamine and using 27.3 g. of 3-(4bromobenzoyl)propionic acid, hydroxysuccinimide ester 13.0 g. of methylproline hydrochloride and 150 ml. of acetonitrile. The desired product is recovered as 16.6 g. of white crystals, m.p. 83°–85° C.

EXAMPLE 30

1-[3-(4-Bromobenzoyl)-3-bromopropionyl]-L-proline methyl ester

To a solution of 3.52 g. of 1-[3-(4-bromobenzoyl)propionyl]-L-proline methyl ester (Example 29) in 50 ml. of carbon tetrachloride is added dropwise a solution of 0.51 ml. of bromine in 20 ml. of carbon tetrachloride. After 30 minutes 2 drops of 30% hydrobromic acid in acetic acid is added and the mixture is stirred at room temperature for 2 hours. The solvent is decanted from the resulting gum. The gum is dissolved in dichloromethane, washed twice with water, once with sodium chloride solution, dried over magnesium sulfate and clarified with charcoal. The filtrate is evaporated to dryness in vacuo giving the desired product as 3.87 g. of a gum.

EXAMPLE 31

2-[α-[(2-Carboxy-1-pyrrolylcarboxyl)methyl]phenacylthio]-1-methylpyridinium bromide, methyl ester To a solution of 7.5 g. of 1-[3-(4-bromobenzoyl)-3-bromopropionyl]-L-proline in 50 ml. of acetonitrile is added a solution 2.1 g. of 1-methyl-2-(1H)-pyridinethione in 30 ml. of acetonitrile. The mixture is stirred at room temperature for 18 hours and the solvent removed under vacuum to give a white glass. The glass is triturated with ether, filtered and the solid washed with ether and petroleum ether (b.p. 30°-60° C.) to give 8.0 g. of the product as a cream colored powder.

EXAMPLE 32

1-[3-(4-Bromobenzoyl)-3-thiopropionyl]-L-proline

A 5.2 g. portion of 2-[α-[(2-carboxy-1-pyrrolylcarboxy)methyl]phenacylthio]-1-methylpyridinium bromide, methyl ester (Example 31) is slurried with 50 ml. of water and extracted with chloroform. The extract is evaporated to a gum which is combined with 50 ml. of 1 N sodium hydroxide and stirred at room temperature for 3 hours. The mixture is washed with chloroform and the alkaline solution rendered acidic with hydrochloric acid and extracted with chloroform. This extract is dried and then evaporated to dryness in vacuo giving a glass. The glass is rubbed to a solid with hexane giving a tan amorphous solid. This solid is partition chromatographed on celite using a heptane-ethyl acetate-methanol-water (55:45:15:1) system. Cut number 3 gives the desired product as 539 mg. of a tan glass.

EXAMPLE 33

1-[3-Acetylthio-3-(4-bromobenzoyl)propionyl]-L-proline methyl ester

To a solution of 5.28 g. of 1-[3-(4-bromobenzoyl)-3-bromopropionyl)-L-proline methyl ester (Example 30) in 35 ml. of acetonitrile is added 1.48 g. of potassium thioacetate. The mixture is stirred at room temperature for 2 hours, filtered and the filtrate is evaporated to dryness in vacuo leaving an amber gum. This is dissolved in ether and chromatographed on a 1"×16" silica gel column, eluting with ether and taking 100 ml. cuts. Cut number 3 gives the desired product (1.64 g.) as a glass.

EXAMPLE 34

1-[3-Benzoyl-3-thiopropionyl]-L-proline

To a solution of 65 mg. of hydroxylamine hydrochloride in 10 ml. of methanol is added a solution of 0.35 g. of 1-(3-benzoylthio-3-benzoylpropionyl)-L-proline in 10 ml. of methanol. To the mixture is added 164 mg. of sodium acetate and the mixture is stirred 2 hours. The solvent is removed and the residue partitioned between water and dichloromethane. The organic layer is washed with water, saturated sodium chloride solution and dried over magnesium sulfate. The solvent is removed under vacuum to give 174 mg. of gum. Chromatography over silica gel with solvent ethyl acetate:hexane:acetic acid (75:25:2) gives the product of the Example as a glass.

EXAMPLE 35

1-[3-(4-Bromobenzoyl)propionyl]-L-proline

A mixture of 2.64 g. of 1-[3-(4-bromobenzoyl)propionyl]-L-proline methyl ester (Example 26) and 26 ml. of 1 N sodium hydroxide is stirred at room temperature. The solids are collected by decantation, dissolved in tetrahydrofuran and returned to the alkaline solution which is stirred further at room temperature. This alkaline solution is washed with ethyl acetate and poured into iced hydrochloric acid. This mixture is extracted with dichloromethane. The organic extract is dried over magnesium sulfate and evacuated to dryness in vacuo leaving a gum. This gum is triturated with ether giving white crystals which are recrystallized from acetone-hexane giving the desired product as 1.35 g. of white crystals, mp. 138°-139° C.

EXAMPLE 36

1-[3-(4-Bromobenzoyl)propionyl]-L-proline

To a solution of 12.65 g. of proline and 18.5 g. of sodium bicarbonate in 390 ml. of water is added a slurry of 39.0 g. of 1-(3-p-bromobenzoyl)propionic acid hydroxysuccinimide ester (Example 27) in 390 ml. of ethanol. The mixture is stirred at room temperature for 18 hours, evaporated to ½ its volume and acidified with concentrated hydrochloric acid producing an oil. This oil crystallizes, with rubbing, to a solid which is recrystallized from acetone-hexane giving the desired product as 26.3 g. of tan needles, mp. 143°-144° C.

EXAMPLE 37

1-[3-(4-Bromobenzoyl)-3-bromopropionyl]-L-proline

To a solution of 17.7 g. of 1-[3-(4-bromobenzoyl)propionyl]-L-proline (Example 36) in 150 ml. of acetic acid is added dropwise, a solution of 9.0 g. of bromine in 20 ml. of acetic acid followed by 5 drops of hydrobromic acid in acetic acid. The mixture is stirred for 18 hours, evaporated to ½ its volume, poured into 300 ml. of ice water and extracted with methylene chloride. The organic extract is washed twice with water, once with saturated sodium chloride solution, dried over magnesium sulfate, clarified with charcoal and evaporated to dryness in vacuo. The desired product is recovered as 20.5 g. of a white amorphous solid.

EXAMPLE 38

1-[3-Acetylthio-3-(4-bromobenzoyl)propionyl]-L-proline

To a stirred suspension of 469 mg. of potassium thioacetate in 10 ml. of ethanol is added 1.76 g. of 1-[3-(4-bromobenzoyl)-3-bromopropionyl]-L-proline (Example 37). The mixture is stirred at room temperature for 18 hours, filtered and the filtrate evaporated to dryness. The residue is dissolved in dichloromethane, washed with water and saturated sodium chloride solution, dried over magnesium sulfate and evaporated to dryness in vacuo giving the desired product as 1.68 g. of a white glass.

EXAMPLE 39

1-[3-(4-Bromobenzoyl)-3-benzoylthiopropionyl]-L-proline

To 440 mg. of sodium hydride in oil dispersion is added a solution of 1.60 g. of thiobenzoic acid in 25 ml. of ethanol. The mixture is stirred for 30 minutes and then 4.33 g. of 1-[3-(4-bromobenzoyl)-3-bromopropionyl]-L-proline (Example 37) is added and the mixture is stirred at room temperature for 18 hours, the solvent is removed in vacuo and the residue is partitioned between dichloromethane and water. The organic layer is washed with water, then sodium chloride solution, dried over magnesium sulfate and evaporated to dryness in vacuo leaving a peach colored glass. A 2.8 g. portion of this glass is dissolved in ethyl acetate-hexane-acetic acid (75:25:2) and placed on a 1"×15" column of silica gel. The column is eluted with the same solvent system (100 ml. hold back volume) taking 50 ml. cuts. The desired product is recovered in cut number 2 as a glass.

EXAMPLE 40

4-Benzoylbutyric acid hydroxysuccinimide ester

To a partial solution of 25 g. of 4-benzoylbutyric acid in 200 ml. of dioxane is added 14.45 g. of N-hydroxysuccinimide. The mixture is stirred and a solution of 26.8 g. of dicyclohexylcarbodiimide in 100 ml. of dioxane is added dropwise. The mixture is stirred for 18 hours, filtered and the filtrate is evaporated to an oil. This oil is rubbed to a solid with hexane. The solid is recrystallized from dichloromethane-hexane with chilling, giving the desired product as 24.6 g. of white crystals, mp. 117°–120° C.

EXAMPLE 41

1-(4-Benzoylbutyryl)-L-proline

To a stirred solution of 9.78 g. of proline and 14.3 g. of sodium bicarbonate in 340 ml. of water is added a partial solution of 24.6 g. of 4-benzoylbutyric acid hydroxysuccinimide ester (Example 40) in 340 ml. of ethanol. The mixture is stirred for 18 hours, evaporated to ½ its volume and acidified with concentrated hydrochloric acid in an ice bath. The mixture is extracted with dichloromethane. The organic extract is washed with water and saline, dried over magnesium sulfate and evaporated in vacuo to a gum. The gum is rubbed to a solid with hexane containing a little dichloromethane. The solid is dissolved in 100 ml. of warm acetone, filtered and 150 ml. of hexane is added. The mixture is stirred in an ice bath, giving the desired product as 14.9 g. of white crystals, mp. 102°–105° C.

EXAMPLE 42

1-(4-Bromo-4-benzoylbutyryl)-L-proline

To a solution of 11.5 g. of 1-(4-benzoylbutyryl)-L-proline (Example 41) in 115 ml. of acetic acid is added dropwise a solution of 6.4 g. of bromine in 25 ml. of acetic acid. The mixture is stirred for 18 hours, reduced to ⅓ its volume, poured into ice and water and extracted with dichloromethane. The organic extract is washed with water and saline, dried over magnesium sulfate and evaporated in vacuo to a yellow gum. This gum is dissolved in dichloromethane, placed on a 1½"×24" column of silica gel which has been wet with dichloromethane and eluted with ethyl acetate:acetic acid (1:1) taking 100 ml. cuts. Cut number 7 gives 2.1 g. of solid which is dissolved in dichloromethane, filtered through celite and evaporated to dryness giving the desired product as 2.0 g. of an orange gum.

EXAMPLE 43

1-(4-Acetylthio-4-benzoylbutyryl)-L-proline

To a solution of 2.0 g. of 1-(4-bromo-4-benzoylbutyryl)-L-proline (Example 42) in 20 ml. of ethanol is added 752 mg. of potassium thioacetate. The mixture is stirred at room temperature for 18 hours, evaporated to dryness and the residue is partitioned between dichloromethane and water. The dichloromethane layer is separated, washed with saline, dried over magnesium sulfate, treated with charcoal and evaporated to a gum. This gum is dissolved in ethyl acetate-hexane-acetic acid (75:25:2) and chromatographed on a 1"×15" silica gel column (100 ml. hold back volume) taking 50 ml. cuts. Cuts 3–6 are combined to give the desired product.

EXAMPLE 44

1-[3-(3-Fluorobenzoyl)-2-methylpropionyl]-L-proline methyl ester

To a solution of 2.10 g. of 3-(4-fluorobenzoyl)-2-methylpropionic acid (Example 2) in 20 ml. of tetrahydrofuran is added 1.62 g. of 1,1'-carbonyldiimidazole. The mixture is stirred at room temperature for one hour, then 1.66 g. of L-proline methyl ester is added and stirring is continued for 18 hours. The mixture is evaporated to dryness in vacuo and the residue is partitioned between dichloromethane and water. The organic layer is separated and washed successively with 1 N hydrochloric acid, water, sodium bicarbonate solution and saline, dried over magnesium sulfate and evaporated to dryness in vacuo giving the desired product as 1.98 g. of a gum.

EXAMPLE 45

1-[3-(3-Fluorobenzoyl)-2-methylpropionyl]-L-proline

A 1.98 g. portion of 1-[3-(3-fluorobenzoyl)-2-methylpropionyl]-L-proline methyl ester (Example 44) is dissolved in 2 ml. of tetrahydrofuran and 20 ml. of 1 N sodium hydroxide is added. The mixture is stirred at room temperature for 4 hours, cooled in an ice bath, acidified with concentrated hydrochloric acid and extracted with dichloromethane. The organic extract is washed with sodium chloride solution, dried over magnesium sulfate and evaporated in vacuo to a gum. This gum is triturated with ether giving the desired product as 500 mg. of a white solid.

EXAMPLE 46

3-(3-Chlorobenzoyl)-2-methylpropionic acid

To a solution of 11.8 g. of α-(3-chlorophenyl)-4-morpholineacetonitrile in 50 ml. of tetrahydrofuran is added 60 drops of a 30% solution of potassium hydroxide in methanol. To the solution is added 4.62 ml. of methacrylonitrile. After stirring one hour, the mixture is concentrated to dryness and the residue dissolved in dichloromethane. The solution is passed through a short column of hydrous magnesium silicate and the eluent concentrated to give 15.5 g. of a yellow oil. The oil is heated on a steam bath with a mixture of 75 ml. of acetic acid and 5 ml. of water for one hour. The solvent is removed under vacuum and water added to the residue. Filtration gives 11.2 g. of 3-(3-chlorobenzoyl)-2-methylpropionitrile as crystals, mp. 72°–75° C.

A mixture of the preceding compound (7.9 g.) and 75 ml. of concentrated hydrochloric acid is refluxed for one hour. The mixture is cooled and filtered to give 8.5 g. of the product of the Example as crystals, mp. 102°–105° C.

EXAMPLE 47

3-(4-Chlorobenzoyl)-2-methylpropionic acid

To a mixture of 152.2 g. of p-toluenesulfonic acid and 148.1 g. of morpholine in 700 ml. of tetrahydrofuran is added 102 g. of 4-chlorobenzaldehyde in 200 ml. of tetrahydrofuran. The mixture is refluxed for 6 hours, cooled and 65.1 g. of potassium cyanide in 100 ml. of water is added. The mixture is refluxed for 18 hours and the solvent is removed under vacuum. The residue is dissolved in dichloromethane and the solution washed with sodium bisulfite solution and passed through a column of hydrous magnesium silicate. The filtrate is concentrated to near dryness and hexane added. Filtration gives 87.5 g. of α-(4-chlorophenyl)-4-morpholineacetonitrile as white crystals, mp. 70° C. To the preceding compound (87.5 g.) in 500 ml. of tetrahydrofuran is added 25 ml. of a 30% solution of potassium hydroxide in ethanol. To the mixture is added 33.5 ml. of methacrylonitrile. The mixture is stirred 50 hours at room temperature and the solvent removed under vacuum. The residue is dissolved in dichloromethane and passed through a column of hydrous magnesium silicate. The eluate is concentrated and diluted with hexane to give 50 g. of white crystals, mp. 158°–160° C.

A mixture of the preceding compound (50 g.) in 400 ml. of acetic acid and 100 ml. of water is refluxed for 18 hours. The solvent is removed and the residue dissolved in dichloromethane. The solution is passed through a column of hydrous magnesium silicate and the eluate concentrated to give a yellow oil. Crystallization from hexane gives 57 g. of 3-(4-chlorobenzoyl)-2-methylpropionitrile as crystals, mp. 80°–82° C.

The preceding compound is refluxed with concentrated hydrochloric acid to give the product of the Example, mp. 125°–129° C.

EXAMPLE 48

1-[3-Acetylthio-3-(1-naphthoyl)-2-methylpropionyl]-L-proline

To a mixture of 133.2 g. of p-toluenesulfonic acid and 130.7 g. of morpholine in 500 ml. of tetrahydrofuran is added 98.0 g. of 1-naphthaldehyde and the mixture is refluxed for 6 hours. To the cooled mixture is added 48.8 g. of potassium cyanide in 100 ml. of water and the mixture is refluxed 18 hours. The solvent is removed and the residue partitioned between dichloromethane and water. The organic layer is separated and the aqueous layer extracted with dichloromethane. The organic layer and extracts are combined, washed with saturated sodium bisulfite solution and passed through a column of hydrous magnesium silicate. The eluent is concentrated, diluted with hexane and filtered to give 123 g. of α-(1-naphthyl)-4-morpholineacetonitrile as crystals, mp. 88°–89° C.

To the preceding compound (120 g.) in 500 ml. of tetrahydrofuran is added 35 ml. of a 30% solution of potassium hydroxide in ethanol and 43.6 ml. of methacrylonitrile. The mixture is stirred at room temperature for 24 hours and the solvent removed. To the residue is added 600 ml. of 6 N hydrochloric acid and the mixture refluxed 18 hours. The mixture is extracted with dichloromethane and the organic extract extracted with sodium bicarbonate solution. The aqueous layer is acidified with hydrochloric acid and extracted with dichloromethane. The dichloromethane extract is washed with saturated sodium chloride solution and dried over magnesium sulfate. The solvent is removed and the residue triturated with hexane to give 19.2 g. of 3-(1-naphthoyl)-2-methylpropionic acid as crystals, mp. 111°–114° C.

The preceding compound (12.0 g.) is dissolved in 100 ml. of dioxane and 5.70 g. of N-hydroxysuccinimide added. To the mixture is added 10.2 g. of N,N-dicyclohexylcarbodiimide in 100 ml. of dioxane over a 15 minute period. The mixture is stirred overnight, filtered and the filter cake washed with dioxane. The filtrate is concentrated, hexane added and filtered. The solid is recrystallized from dichloromethane-hexane to give 3-(1-naphthoyl)-2-methylpropionic acid, hydroxysuccinimide ester as white crystals, mp. 170° C.

The preceding compound (3.4 g.) is slurried in 40 ml. of ethanol and added to a solution of 2.30 g. of L-proline and 1.68 g. of sodium carbonate in 40 ml. of water. The mixture is stirred at room temperature for one week. The mixture is concentrated to ½ volume, chilled and acidified with concentrated hydrochloric acid. The mixture is extracted with dichloromethane and the extract washed with saturated sodium chloride solution and dried over magnesium sulfate. The solvent is removed to give 1-[3-(1-naphthoyl)-2-methylpropionyl]-L-proline.

The preceding compound is separated into diastereoisomers A and B and each is reacted with bromine as in Example 19 to give 1-[3-bromo-3-(1-naphthoyl)-2-methylpropionyl]-L-proline as a glass (brominated isomer A and brominated isomer B). The preceding compounds are reacted with potassium thioacetate as in Example 21 to give the products of the Example.

EXAMPLE 49

1-[3-Acetylthio-3-(3-chlorobenzoyl)propionyl]-L-proline

To a cold solution of 76 g. of p-toluenesulfonic acid in 500 ml. of tetrahydrofuran is added 87 g. of morpholine and 50.6 g. of m-chlorobenzaldehyde. The mixture is refluxed for 2.5 hours and 100 ml. of tetrahydrofuran is distilled off. The mixture is cooled and a solution of 28.6 g. of potassium cyanide in 100 ml. of water added. The mixture is refluxed for 5 hours and concentrated to dryness under vacuum. The residue is dissolved in dichloromethane and the solution washed with water, sodium bisulfite solution, saturated sodium chloride solution and dried over magnesium sulfate. The solution is passed through a short column of hydrous magnesium silicate. The eluent is refluxed while hexane is added until crystals separate. Cooling and filtering gives 78 g. of α-(3-chlorophenyl)-4-morpholineacetonitrile as crystals, mp. 72°–73° C.

To the preceding compound (23.6 g.) in 100 ml. of tetrahydrofuran is added 120 drops of a 30% solution of potassium hydroxide in methanol. To the mixture is added 4.1 ml. of acrylonitrile. After stirring one hour, the mixture is concentrated to dryness under vacuum. The residue is dissolved in dichloromethane and passed through a short column of hydrous magnesium silicate. The eluent is concentrated under vacuum to give 36.6 g. of yellow oil. The oil is heated on a steam bath with a mixture of 150 ml. of acetic acid and 10 ml. of water for one hour. The solvent is removed under vacuum and the residue treated with water. The mixture is filtered to give 18.8 g. of 3-(3-chlorobenzoyl)propionitrile as crystals, mp. 49°–51° C.

A mixture of the preceding compound (8.1 g.) and 80 ml. of concentrated hydrochloric acid is refluxed for 7 hours. Cooling gives an oil which crystallizes to give 8.8 g. of 3-(3-chlorobenzoyl)propionic acid as crystals, mp. 105°–107° C.

The preceding compound is converted to 3-[3-chlorobenzoyl]propionic acid, hydroxysuccinimide ester as described in Example 15 and coupled with L-proline as described in Example 16 to give 1-[3-(3-chlorobenzoyl)propionyl]-L-proline. The preceding compound is reacted with bromine in acetic acid as described in Example 20 to give 1-[3-bromo-3-(3-chlorobenzoyl)propionyl]-L-proline. The preceding compound in a mixture of ethanol-water (1:1) is reacted with potassium thioacetate as in Example 21 to give the product of the Example as a glass.

EXAMPLE 50

1-[3-Acetylthio-3-(4-tert-butylbenzoyl)propionyl]-L-proline

To a stirred mixture of 17.0 g. of p-tert-butylbenzene and 13.0 g. of succinic anhydride in 340 ml. of 1,1,2,2-tetrachloroethane is added 36 g. of aluminum chloride. The mixture is stirred at room temperature for 3 hours. The mixture is poured into 170 ml. of ice cold 6 N hydrochloric acid. The mixture is evaporated at room temperature overnight and the residual slush is stirred with 300 ml. of boiling water, cooled and filtered. The solid is dissolved in 1.5 liters of boiling water containing 20 g. of sodium carbonate. The hot mixture is filtered and the filtrate acidified with 100 ml. of 6 N hydrochloric acid. Chilling and filtering gives a tan solid which is recrystallized from ethanol-water to give 28 g. of product, mp. 85°–89° C. Recrystallization from benzene-petroleum ether gives 17.0 g. of 3-(4-tert-butylbenzoyl)-propionic acid as light yellow crystals, mp. 119°–121° C.

The preceding compound is converted to 3-(4-tert-butylbenzoyl)propionic acid hydroxysuccinimide ester as described in Example 15 which is coupling with L-proline to give 1-[3-(4-tert-butylbenzoyl)propionyl]-L-proline.

The preceding compound is reacted with bromine in acetic acid to give 1-[3-bromo-3-(4-tert-butylbenzoyl)-propionyl]-L-proline as described in Example 20.

The preceding compound in a mixture of ethanol-water (1:1) is reacted with potassium thioacetate as in Example 21 to give the product of the Example as a glass.

EXAMPLE 51

1-[3-Acetylthio-3-(3-trifluoromethylbenzoyl)propionyl]-L-proline

To a solution of 5.0 g. of α-[3-(trifluoromethyl)-phenyl]-4-morpholineacetonitrile in 200 ml. of tetrahydrofuran stirred at room temperature is added 30 drops of 30% potassium hydroxide in ethanol. To the mixture is added 10 ml. of ethyl acrylate. After one hour an additional 30 drops of 30% potassium hydroxide in ethanol and 10 ml. of ethyl acrylate is added. The mixture is stirred for 2 hours and the solvent removed under vacuum. Toluene is added several times and the solvent removed. The residue is stirred with ether, filtered and the solvent evaporated to give ethyl γ-cyano-γ-[3-(trifluoromethyl)phenyl]-4-morpholinebutanoate (5.6 g.) as an oil. The oil is heated with 70% glacial acetic acid for 2 hours and the solvent removed. The residue is dissolved in dichloromethane and washed with water. The organic layer is dried ($Na_2SO_4$) and the solvent removed to give an oil. A mixture of the oil and 300 ml. of 6 N hydrochloric acid is refluxed for 5 hours, cooled and extracted with dichloromethane. The organic layer is extracted with sodium bicarbonate. The aqueous layer is acidified with concentrated hydrochloric acid and extracted with dichloromethane. The extract is dried ($Na_2SO_4$) and the solvent removed. The residue is crystallized from hexane to give 3-[3-trifluoromethylbenzoyl]propionic acid as crystals, mp. 80°–82° C.

As described in Example 15, 3-(3-trifluoromethylbenzoyl)propionic acid, hydroxysuccinimide ester is prepared and coupled to L-proline as in Example 16. The 1-[3-(3-trifluoromethylbenzoyl)propionyl]-L-proline in acetic acid is reacted with bromine as in Example 20 to give 1-[3-bromo-3-(3-trifluoromethylbenzoyl)propionyl]-L-proline. The preceding compound is reacted with potassium thioacetate in ethanol-water (1:1) as in Example 21 to give the product of the Example as a glass.

EXAMPLE 52

1-[3-Acetylthio-3-(3,4-dichlorobenzoyl)propionyl]-L-proline

To a mixture of 122 ml. of morpholine and 124 g. of p-toluenesulfonic acid in 150 ml. of tetrahydrofuran is added 106.3 g. of 3,4-dichlorobenzaldehyde in 50 ml. of tetrahydrofuran. The mixture is heated on a steam bath for 2 hours. To the mixture is added a slurry of 45 g. of potassium cyanide in 30 ml. of water. The mixture is refluxed for 2 hours and the solvent removed under vacuum. To the residue is added a solution of sodium bisulfite and the mixture is extracted with dichloromethane. The extract is washed with sodium bisulfite solution and dried over magnesium sulfate. The solvent is removed under vacuum. The residue is dissolved in benzene and diluted with petroleum ether to give 122 g. of α-(3,4-dichlorophenyl)-4-morpholineacetonitrile as crystals, mp. 59°–60° C.

The preceding compound (11.6 g.) is dissolved in 125 ml. of tetrahydrofuran and 60 drops of a solution of 30% potassium hydroxide in ethanol added. To the mixture is added dropwise 6.8 ml. of ethyl acrylate in 50 ml. of tetrahydrofuran over 10 minutes. After 1.5 hours at room temperature, the solvent is removed under vacuum. Toluene is added and the solvent removed. A mixture of petroleum ether-ether is added and the mixture filtered. The filtrate is concentrated to give 12.9 g. of yellow oil. The oil is heated with 70% acetic acid on a steam bath for 2 hours. The solvent is removed to give ethyl 3-(3,4-dichlorobenzoyl)propionate.

The preceding compound is heated with 6 N hydrochloric acid to give 3-(3,4-dichlorobenzoyl)propionic acid. As described in Example 15, 3-(3,4-dichlorobenzoyl)propionic acid, hydroxysuccinimide ester is prepared and coupled to L-proline as in Example 16. The 1-[3-(3,4-dichlorobenzoyl)propionyl]-L-proline in acetic acid is reacted with bromine as in Example 20 to give 1-[3-bromo-3-(3,4-dichlorobenzoyl)propionyl]-L-proline.

The preceding compound is reacted with potassium thioacetate in ethanol-water (1:1) as in Example 21 to give the product of the Example as a glass.

EXAMPLE 53

1-[3-Acetylthio-3-(4-chloro-3-trifluoromethylbenzoyl)propionyl]-L-proline

A 48.9 g. sample of 5-amino-2-chlorobenzotrifluoride is converted to 4-chloro-3-trifluoromethylbenzaldehyde according to the procedure described in Organic Synthesis Coll., Vol. 5, p. 139, to give 13.9 g. of oil.

The preceding compound (13.9 g.) is added to a mixture of 14.3 g. of p-toluenesulfonic acid and 13.0 g. of morpholine in 150 ml. of tetrahydrofuran. The mixture is refluxed for 3 hours and 4.9 g. of potassium cyanide in 25 ml. of water added. The mixture is refluxed for 18 hours and the solvent is removed under vacuum. The residue is diluted with water and extracted with dichloromethane. The extract is washed with saturated sodium bisulfite solution and saturated saline solution and passed through a column of hydrous magnesium silicate. The filtrate is concentrated under vacuum and the residue crystallized from dichloromethane-hexane to give 14 g. of 60 -(4-chloro-3-trifluoromethylphenyl)-4-morpholineacetonitrile as crystals, mp. 73°–74° C.

To the preceding compound (14 g.) in 150 ml. of tetrahydrofuran is added one ml. of a solution of 30% potassium hydroxide in methanol. To the mixture is added 10 ml. of methyl acrylate and the mixture is allowed to stand at room temperature overnight. The solvent is removed under vacuum and the residue stripped with toluene several times. The residue is dissolved in dichloromethane and passed through a column of hydrous magnesium silicate. The filtrate is concentrated to give an oil. The oil is heated with 70% acetic acid on a steam bath and hydrolyzed with 6 N hydrochloric acid as described in Example 51 to give 3-(4-chloro-3-trifluoromethylbenzoyl)propionic acid as described in Example 15.

The preceding compound is converted to 3-(4-chloro-3-trifluoromethylbenzoyl)propionic acid, hydroxysuccinimide ester and coupled to L-proline as in Example 16. The 1-([3-(4-chloro-3-trifluoromethylbenzoyl)propionyl]-L-proline is brominated as in Example 20 and the product reacted with potassium thioacetate in ethanol-water (1:1) as in Example 21 to give the product of the Example as a glass.

EXAMPLE 54

1-[3-Acetylthio-3-(3-fluoro-4-methoxybenzoyl)propionyl]-L-proline

As described in Example 52, 3-fluoro-4-methoxybenzaldehyde is converted to 3-(3-fluoro-4-methoxybenzoyl)propionic acid, mp. 169°–171° C.

As described in Example 15, the preceding compound is converted to 3-(3-fluoro-4-methoxybenzoyl)propionic acid, hydroxysuccinimide ester and coupled to L-proline as in Example 16. The 1-[3-(3-fluoro-4-methoxybenzoyl)propionyl]-L-proline m.p. 180°–182° C. is brominated as in Example 20 and the product reacted with potassium thioacetate in ethanol-water as in Example 21 to give the product of the Example as a glass.

EXAMPLE 55

1-[3-Acetylthio-3-(3-fluorobenzoyl)-2-methylpropionyl]-L-proline

To a solution of 6.21 g. of proline and 9.07 g. of sodium bicarbonate in 220 ml. of water is added a slurry of 16.6 g. of 1-[3-bromo-3-(3-fluorobenzoyl)-2-methylpropionyl]-L-proline in 220 ml. of ethanol. The mixture is stirred at room temperature for 18 hours and filtered. The filtrate is concentrated under vacuum to ½ volume, cooled in an ice bath, filtered and acidified with concentrated hydrochloric acid (approximately pH 4). The mixture is extracted with dichloromethane and the extract washed with water, saturated sodium chloride solution and dried over magnesium sulfate. The solvent is removed to give 11.8 g. of white gum. The gum is dissolved in one ml. of ethyl acetate, 10 ml. of hexane and 0.2 ml. of acetic acid. Chilling and filtering gives 3.18 g. of white crystals, mp. 176°–180° C. (labeled isomer A). The filtrate is chromatographed twice over silica gel solvent-ethyl acetate-hexane-acetic acid (25:25:1) to give 3.2 g. of a gum (labeled isomer B).

Isomer A is reacted with N,N-dicyclohexylamine in acetone to give the dicyclohexylamine salt of isomer A, mp. 164°–166° C.

Isomer B is reacted with N,N-dicyclohexylamine in acetone to give the dicyclohexylamine salt of isomer B, mp. 98°–100° C.

A 6.8 g. sample of isomer B as its dicyclohexylamine salt is dissolved in 50 ml. of water, chilled and acidified with concentrated hydrochloric acid. The mixture is extracted with ethyl acetate and the extract concentrated to give 4.3 g. of gum. The gum is dissolved in 20 ml. of methanol and 20 ml. of water and 4 ml. of 1 N sodium hydroxide is added. This solution is passed through 50 g. of IR-120 resin (prewashed with 1 N hydrochloric acid and then water). The cuts containing solid are combined and the solids partitioned between dichloromethane and water. The dichloromethane layer is washed with water, saturated sodium chloride solution and dried over magnesium sulfate. The solvent is removed to give 3.3 g. of gum which is crystallized from hexane and a trace of ether to give 3.07 g. of white crystals, mp. 100°–103° C. Recrystallization from ethyl acetate-hexane gives 1.5 g. of crystals, mp. 107°–108° C. (pure isomer B).

To a solution of 4.0 g. of isomer A (mp. 184°–186° C.) in 90 ml. of acetic acid is added 2.08 g. of bromine in 10 ml. of acetic acid. After 18 hours at room temperature, the solution is concentrated to ½ volume and poured into ice and water. The mixture is extracted with dichloromethane and the extract concentrated to dryness to give 4.78 g. of 1-[3-bromo-3-(3-fluorobenzoyl)-2-methylpropionyl]-L-proline as a glass (bromo derivative from isomer A).

To a solution of 2.32 g. of this bromo derivative from isomer A in 25 ml. of ethanol is added 0.82 g. of potassium thioacetate and the mixture is stirred at room temperature for 42 hours. The solvent is removed and the residue partitioned between water and dichloromethane. The organic layer is washed with water and saturated sodium chloride solution and dried over magnesium sulfate. The solvent is removed to give 2.06 g. of solid. Purification by chromatography on silica gel with solvent ethyl acetate-hexane-acetic acid (25:25:1) gives 0.52 g. of solid. Crystallization from ethyl acetate-hexane gives 0.3 g. of product as crystals, mp. 113°–115° C. (product from isomer A).

In a similar manner as described above, the isomer B is brominated to give 1-[3-bromo-3-(3-fluorobenzoyl)-2-methylpropionyl]-L-proline as a glass (brominated derivative from isomer B). This brominated derivative from isomer B is reacted with potassium thioacetate in ethanol to give the product of the Example derived from isomer B.

EXAMPLE 56

Preparation of 50 mg. Tablets

| Per Tablet | | Per 10,000 Tablets |
|---|---|---|
| 0.050 gm. | 1-[3-(m-fluorobenzoyl)-2-acetylthiopropionyl]-L-proline | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 1-[3-(m-fluorobenzoyl)-2-acetylthiopropionyl]-L-proline, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 57

Preparation of Oral Suspension

| Ingredient | Amount |
|---|---|
| 1-[3-(3,4-dimethoxybenzoyl)-2-benzoylthiopropionyl]-L-proline | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs to | 100 ml. |

The sorbitol solution is added to 40 ml. of distilled water and the 1-[3-(3,4-dimethoxybenzoyl)-2-benzoylthiopropionyl]-L-proline is suspended therein. The saccharin, sodium benzoate, flavor and dye are added and dissolved. The volume is adjusted to 100 ml. with distilled water. Each ml. of syrup contains 5 mg. of 1-[3-(3,4-dimethoxybenzoyl)-2-benzoylthiopropionyl]-L-proline.

EXAMPLE 58

Preparation of Parenteral Solution

In a solution of 700 ml. of propylene glycol and 200 ml. of water for injection is suspended 20.0 grams of 1-[3-(4-trifluoromethylbenzoyl)-2-mercaptopropionyl]-L-proline, sodium salt with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 59

1-[3-Acetylthio-5-(4-methoxy-1-naphthoyl)propionyl]-L-proline 3-(4-Methoxy-1-naphthoyl)propionic acid is coupled to L-proline as described in Examples 15 and 16 to give 1-[3-(4-methoxy-1-naphthoyl)propionyl]-L-proline. The preciding compound is reacted with bromine in acetic acid as in Example 26 and the product reacted with potassium thioacetate in ethanol to give the product of the Example as a glass.

EXAMPLE 60

1-[3-Acetylthio-3-(3,4,5-trimethoxybenzoyl)propionyl]-L-proline

As described in Example 52, 3,4,5-trimethoxybenzaldehyde is converted to 3-(3,4,5-trimethoxybenzoyl)propionic acid. The preceding compound is converted to the hydroxysuccinimide ester as described in Example 15 and coupled to L-proline as described in Example 16. The 1-[3-(3,4,5-trimethoxybenzoyl)propionyl]-L-proline is reacted with bromine in acetic acid as in Example 20 to give 1-[3-bromo-3-(3,4,5-trimethoxybenzoyl)propionyl]-L-proline. The preciding compound is reacted with potassium thioacetate in ethanol-water as in Example 21 to give the product of the Example as a glass.

EXAMPLE 61

1-[3-Acetylthio-3-(4-biphenylylcarbonyl)propionyl]-L-proline

A mixture of 50.0 g. of 3-(biphenylylcarbonyl) propionic acid, 23.0 g. of N-hydroxysuccinimide, 41.3 g. of N,N-dicyclohexylcarbodiimide and 400 ml. of dioxane is stirred at room temperature. The mixture is filtered and the filtrate concentrated to an oil which is crystallized from chloroform-hexane to give 38 g. of crystals, m.p. 160°–163° C. Recrystallization from chloroform-ethanol gives 32 g. of cream colored crystals, m.p. 163°–164° C. A mixture of the preceding compound (20 g), 9.9 g. of L-proline, 14.3 sodium bicarbonate and 170 ml. of water and 200 ml. of ethanol is stirred at room temperature and concentrated to ½ volume. The mixture is acidified with concentrated HCl and filtered to give 24.0 g. of off-white solid. The solid is dissolved in dichloromethane and extracted with aqueous sodium bicarbonate. The aqueous phase is acidified with concentrated HCl, filtered and the solid washed with water to give 10 g. of off-white crystals, m.p. 128°–131° C.

Recrystallization from CH₂Cl₂hexane gives white crystals, m.p. 131°–133° C. The preceding compound (7.0 g) is brominated as described in Example 20 to give 1-[3-bromo-3-(4-biphenylylcarbonyl)propionyl]-L-proline, m.p. 135°–138° C. (2.0 g). The preceding compound (0.50 g) is reacted with sodium thioacetate in 5 ml. of ethanol to give the product of the Example as white crystals, 173°–176° C.

EXAMPLE 62

1-{3-Acetylthio-3-[4-(4-chlorophenoxy)benzoyl]-propionyl}-L-proline

A mixture of 9.8 g. of 3-(4-fluorobenzoyl)propionic acid, 6.5 g. of p-chlorophenol, 13.8 g. of potassium carbonate and 120 ml. of N,N-dimethylacetamide in heated under argon at 135° C. for 16 hours. The mixture is cooled and poured into 1 liter of water. The mixture is filtered through celite and the filtrate acidified with concentrated hydrochloric acid. The mixture is diluted to 2 liters, filtered and the solid recrystallized from ethanol-water (1:1) to give 12.2 g. of colorless needles, m.p. 148°–150° C. The preceding compound is converted to 3-[4-(4-chlorophenoxy)benzoyl]propionic acid hydroxysucciniimide ester as described in Example 15 which is coupled to L-proline to give 1-{3-[4-(chlorophenoxy)benzoyl)benzoyl]propionyl}-L-proline. The preceding compound is reacted with bromine in acetic acid to give 1-{3-bromo-3-[4-(4-chlorophenoxy)benzoyl]propionyl}-L-proline as described in Example 20. The preceding compound in a mixture of ethanol-water is reacted with potassium thioacetate as in Example 21 to give the product of the Example as a glass.

EXAMPLE 63

1-[3-Acetylthio-3-(4-chlorobenzoyl)-2-methylpropionyl]-L-proline

A solution of 14.3 g. of 3-(4-chlorobenzoyl)-2-methylpropionic acid (Example 47), 7.26 g. of N-hydroxysuccinimide and 13 g. of dicyclohexylcarbidiimide in 150 ml. of dioxane is allowed to stir at room temperature overnight and is then filtered. The filtrate is concentrated at reduced pressure and taken up in 100 ml. of water containing 7.25 g. of L-proline and 10.58 g. of sodium bicarbonate. The mixture is stirred at 25°–35° overnight and filtered through celite. The filtrate is concentrated to remove the ethanol. Concentrated hydrochloric acid is added and the mixture is extracted several times with dichloromethane. The extracts are washed with water and dried (Na₂SO₄). Evaporation of the solvent yields an amber gum which is dissolved in ethylacetate. Hexane is added, causing white crystals to separate. Recrystallization from ethylacetate gives colorless needles, m.p. 177.5–179.5, labeled isomer A. The preceding compound is brominated as in Example 20 and the product reacted with potassium thioacetate in ethanol-water as in Example 21 to give the product of the Example as a glass.

EXAMPLE 64

1-[3-Acetylthio-3-(3-fluorobenzoyl)propionyl]-L-proline 3-(3-Fluorobenzoyl)propionic acid is prepared from 3-fluorobenzoldehyde as for Example 47 to give yellow needles m.p. 97°–99° C. To a mixture of the preceding compound (9.8 g) and 5.75 g. of N-hydroxysuccinimide in 80 ml. of dioxane is added a solution of 10.3 g. of N,N-dicyclohexylcarbodiimide in 40 ml. of dioxane. The mixture is stirred at room temperature for 18 hrs., filtered and the solvent removed under vacuum. The residue is triturated with hexane to give 13.7 g. of off-white crystals, m.p. 115°–122° C. Recrystallization from CH₂Cl₂-hexane gives 11 g. of white crystals, m.p. 130°–133° C. The preceding compound (11 g) as a slurry in 210 ml. of ethanol is added to a solution of 9.24 g. of sodium bicarbonate and 6.33 g. of L-proline in 210 ml. of water. After stirring for 18 hrs. at room temperature the solution is concentrated to ½ volume under vacuum, chilled and acidified with concentrated hydrochloric acid. The mixture is extracted with dichloromethane and the extracts washed with water and saline and dried (MgSO₄). The solvent is removed under vacuum to give 10.8 g. of gum. Trituration with hexane containing a trace of ether gives 8.6 g. of white crystals, m.p. 84°–89° C. The preceding compound (6.42 g) is brominated as in Example 20 to give 1-[3-fluorobenzoyl)propionyl]-L-proline as a white glass (7.9 g). The preceding compound (3.72 g) is reacted with 1.48 g. of potassium thioacetate in 35 ml. of ethanol for 18 hrs. to give 3.4 g. of a gum. The gum is chromatographed over silica gel with ethylacetate-hexane-acetic acid (75:25:2) as solvent to give 2.6 g. of the product of the example as a tan glass.

EXAMPLE 65

1-[3-Acetylthio-3-(2-naphthoyl)propionyl]-L-proline

To a solution of 46.8 g. of 2-naphthaldehyde and 57.5 g. of p-toluenesulfonic acid in 300 ml. of tetrahydrofuran is added 52.5 ml. of morpholine. The mixture is refluxed for 1 hour, cooled and a slurry of 19.5 g. of potassium cyanide in 15 ml. of water is added. The mixture is stirred and refluxed for 1 hour, cooled and poured into 600 ml. of 10% potassium carbonate solution. The mixture is extracted with dichloromethane and the extract washed with water, sodium hydrogen sulfite and brine solutions. The solvent is removed under vacuum and the residue triturated with hexane to give 61 g. of yellow solid. The preceding compound (61 g) in 400 ml. of tetrahydrofuran is added 15 ml. of a 30% KOH in ethanol solution. To the mixture is added 24 ml. of acrylonitrile in 150 ml. of tetrahydrofuran. After stirring 24 hours the solvent is removed. The residue is dissolved in CH₂Cl₂ and washed with water and the solution dried (MgSO₄). The solvent is removed under vacuum to give 65 g. of dark gum. To the preceding compound (65 g) is added 230 ml. of acetic acid and 38 ml. of water. The mixture is refluxed for 1.5 hour and the solvent removed. The residue is dissolved in CH₂Cl₂ and washed with water and saline and dried (MgSO₄). The solvent is removed to give 60 g. of dark gum. A mixture of the preceding compound (60 g) and 200 ml. of 6 N hydrochloric acid is refluxed for 1.5 hour. The mixture is chilled, filtered and the solid washed with water to give 49.6 g. of 3-(2-naphthoyl)propionic acid, m.p. 147°–155° C. Recrystallization gives crystals, m.p. 168°–170° C. To a slurry of the preceding compound (9.12 g) in 60 ml. of dioxane is added a solution of 8.24 g. of N,N-dicyclohexylcarbodiiamide in 40 ml. of dioxane and 4.6 g. of N-hydroxysuccinimide. The mixture is stirred at room temperature for 18 hours and filtered. The filtrate is concentrated under vacuum. The residue is triturated with hexane-ether to give 13.0 g. of solid, m.p. 153°–160° C. The solid is dissolved in 150 ml. of CH₂Cl₂ and hexane added (160 ml). Filtering gives 9.8 g. of white crystals, m.p. 162°–165° C. The preceding compound (9.8 g) as a slurry in 160 ml. of ethanol is added to a solution of 5,18 g. of L-proline and 7.58 g. of NaCO$_3$ in 160 ml. of water. The mixture is stirred at room temperature for 18 hours and the solution concentrated to ½ volume. The solution is extracted with ethylacetate and then chilled and acidified with concentrated HCl. The mixture is extracted with CH$_2$Cl$_2$ and the extract washed with H$_2$O and saline and dried (MgSO$_4$). The solvent is removed to give 9.5 g. of gum which is chromatographed over silica gel with ethylacetate-hexane-acetic acid solvent to give 5.5 g. of crystals, m.p. 115°–118° C. The preceding compound, 3-(2-naphthoyl)propionyl-L-proline, (3.24 g) is brominated as Example 20 to give 1-[3-bromo-3-(2-naphthoyl)propionyl]-L-proline as a glass (2.55 g). The preceding compound (2.55 g) in 30 ml. of ethanol is reacted with sodium thioacetate for 18 hours to give the product of the example as a white glass.

EXAMPLE 66

1-[3-Acetylthio-3-(4-chlorobenzoyl)propionyl]-L-proline

To a solution of 34 g. of 1-[3-(4-chlorobenzoyl)propionyl]-L-proline (Example 18) in 300 ml. of acetic acid is added 17.5 g. of bromine. The mixture is stirred 24 hours and the solvent removed under vacuum. The residue is partitioned between dichloromethane and aqueous sodium bicarbonate solution. The aqueous layer is separated and added dropwise onto a mixture of ice and concentrated hydrochloric acid. The mixture is extracted with dichloromethane and the extract dried (Na$_2$SO$_4$). The solvent is removed to give 44 g. of a yellow glass. To a mixture of 0.54 g. of sodium methoxide and 1.14 g. of thioacetic and in 15 ml. of ethanol is added 2.0 g. of the preceding compound and the mixture is stirred for 2 hours. The mixture is poured onto crushed ice and extracted with dichloromethane. The extract is dried (Na$_2$SO$_4$) and the solvent removed under vacuum to give 1.5 g. of the product of the example as a yellow glass.

EXAMPLE 67

1-[3-Benzoylthio-3-(3-fluorobenzoyl)propionyl]-L-proline

A 2.44 g. sample of sodium hydride (60% oil dispersion) is washed with hexane. To the hydride is added 1.6 g. of thiobenzoic acid in 25 ml. of ethanol. To the mixture is added 3.7 g. of 1-[3-bromo-3-(3-fluorobenzoyl)propionyl]-L-proline and the mixture is stirred for 18 hours. The solvent is removed under vacuum and the residue partition between dichloromethane and water. The organic layer is separated, washed with water and saline and dried (MgSO$_4$). The solvent is removed to give 4.5 g. of gum. The gum is chromatographed over silica gel with ethylacetate-hexane-acetic acid as solvent to give 2.5 g. of product as a glass.

EXAMPLE 68

1-[3-(Acetylthio)-3-(2-naphthoyl)propionyl]-L-proline

To a solution of 46.8 g. of 2-naphthaldehyde and 57.5 g. of p-toluenesulfonic acid in 300 ml. of tetrahydrofuran is added 52.5 ml. of morpholine. The mixture is refluxed for one hour, cooled and a slurry of 19.5 g. of potassium cyanide in 15 ml. of water added. The mixture is refluxed for one hour, cooled and poured into 600 ml. of 10% potassium carbonate solution. The mixture is extracted with dichloromethane and the extracts washed with water, 600 ml. of 10% sodium hydrogen sulfite and brine. The extract is dried (MgSO$_4$) and the solvent removed. The residue is triturated with hexane to give 61.7 g. of α-(2-naphthyl)-4-morpholineacetonitrile as yellow solid.

To the preceding solid (61.7 g.) in 400 ml. of tetrahydrofuran is added 15 ml. of 30% KOH in ethanol. To the mixture is added 24 ml. of acrylonitrile in 150 ml. of tetrahydrofuran (exotherm 20° C.→38° C.). The mixture is stirred for 18 hours at room temperature and the solvent removed. The residue is dissolved in dichloromethane and washed with water. The solvent is removed to give 65 g. of dark gum. A mixture of the preceding compound (65 g.), 230 ml. of acetic acid and 38 ml. of water is refluxed for 1.5 hours. The solvent is removed and the residue dissolved in CH$_2$Cl$_2$. The extract is washed with water, saline, and dried (MgSO$_4$) and the solvent removed to give 60 g. of a gum. A mixture of the preceding compound and 200 ml. of 6 N HCl is refluxed 1.5 hours. The mixture is cooled and filtered to give 49.6 g. of crude 3-(2-naphthoyl)propionic acid as a tan solid, m.p. 147°–155° C. The solid is extracted with 500 ml. of hot ethyl acetate. From the ethyl acetate extract is obtained 24.3 g. of crystals in two crops. Recrystallization from (2 times) ethyl acetate gives 10.5 g. of tan crystals, m.p. 168°–170° C.

To a slurry of 9.12 g. of 3-(2-naphthoyl)propionic acid and 4.6 g. of N-hydroxysuccinimide is added 8.24 g. of N,N-dicyclohexylcarbodiimide in 40 ml. of dioxane. The mixture is stirred at room temperature for 18 hours and filtered. The filtrate is concentrated to dryness and the residue triturated with hexane-ether to give 13.0 g. of solid. The solid is dissolved in 150 ml. of dichloromethane and hexane (160 ml.) added. Filtering gives 9.8 g., m.p. 162°–165° C., of N-hydroxysuccinimide ester of 3-(2-napthoyl)propionic acid.

The preceding compound (9.77 g.) as a slurry in 160 ml. of ethanol is added to a solution of 5.18 g. of L-proline and 7.58 g. of sodium bicarbonate in 160 ml. of water. The mixture is stirred at room temperature for 18 hours and the mixture concentrated under vacuum to ½ volume. The mixture is extracted with ethyl acetate and the mixture chilled in an ice bath and acidified with concentrated hydrochloric acid. The acidified mixture is extracted with dichloromethane and the extracts washed with water, brine and dried (MgSO$_4$). The solvent is removed to give 9.5 g. of 1-[3-(2-naphthoyl)propionyl]-L-proline as a gum. chromatography of the gum on a 1.5 inch by 18 inch column of silica gel (60–200 mesh) with ethyl acetate-hexane-acetic acid (1:1:0.4) as solvent gives 5.5 g. of crystals which are recrystallized from dichloromethane-hexane to give 4.9 g. of white crystals, m.p. 116°–118° C.

To 3.24 g. of the preceding compound in 35 ml. of acetic acid is added 1.6 g. of bromine in 10 ml. of acetic acid. The mixture is stirred at room temperature for 18 hours, concentrated to ½ volume under vacuum and poured into ice and water. The mixture is extracted with dichloromethane and the extracts washed with water, saline, and dried (MgSO$_4$). The solvent is removed under vacuum to give 4.0 g. of a gum. The gum is chromatographed over silica gel with ethyl acetate-hexane-acetic acid (1:1:0.4) as solvent. Concentration of column fractions gives 2.6 g. of 1-[3-bromo-3-(2-naphthoyl)propionyl]-L-proline as white amorphous solid, m.p. 50°–80° C.

To 30 ml. of ethanol cooled in an ice bath is added 380 mg. of sodium hydride (60% dispersion in oil), and 0.67 ml. of thiolacetic acid. After stirring for 30 minutes, 2.55 g. of 1-[3-bromo-3-(2-naphthoyl)propionyl]-L-proline is added and the mixture is stirred for 18 hours. The solvent is removed under vacuum. The residue is chromatographed on a silica gel column with ethyl acetate-hexane-acetic acid (7.5:2.5:0.2) as solvent to give 1.2 g. of the product of the example, as a white glass, $[\alpha]_D - 36$(c, 0.96 ethanol).

EXAMPLE 69

[S-(R*,S*)]-1-(3-Acetylthio-3-benzoyl-2-methylpropionyl)-L-proline and
[S-(R*,R*)]-1-(3-acetylthio-3-benzoyl-2-methylpropionyl)-L-proline As described in Example 11, 22.6 g. of (S)-1-(3-benzoyl-2-methylpropionyl)-L-proline (isomer A), m.p. 216°-219° C. in 400 ml. of acetic acid is brominated with 12.5 g. of bromine with the addition of hydrogen bromide gas as a catalyst. After 2 hours the solvent is concentrated to ⅓ volume and poured onto ice and water. The mixture is extracted with dichloromethane and the extracts washed with water, brine and dried (MgSO₄). Concentration of the extract gives a white glass [mixture of [S-(R*,S*)]-1-(3-bromo-3-benzoyl-2-methylpropionyl)-L-proline and [S-(R*,R*)]-1-(3-bromo-3-benzoyl-2-methylpropionyl)-L-proline].

As described in Example 12, 23.9 g. of the preceding compounds (mixture of diastereomers) is reacted with sodium thiolacetate [prepared from 9.0 ml. of thiolacetic acid and 2.92 g. of NaH(60% oil dispersion)] in 2.2 liters of acetonitrile. The mixture is stirred 18 hours at room temperature and 90 ml. of acetic acid added. The solvent is removed under vacuum and the residue partitioned between dichloromethane and water. The organic layer is separated, dried (MgSO₄) and the solvent removed under vacuum to give 23 g. of a gum. The gum is dissolved in hot ethyl acetate and the solution chilled and filtered (2.7 g. of solid). To the filtrate is added 70 ml. of hexane and the solvent decanted from gummy material. The decanted solution is concentrated to give 19.1 g. of gum which is chromatographed on a 2 inch by 25 inch column of silica gel (60–200 mesh) with ethyl acetate-hexane-acetic acid (5:5:0.2). From the first cuts there is obtained 4.53 g. of solid which is crystallized from ethyl acetate-hexane to give 3.14 g. of white crystals, m.p. 123°-125° C. Recrystallization from acetone-hexane gives 3.0 g. of white crystals, m.p. 160°-161° C. of [S-(R*,S*)]-1-(3-acetylthio-3-benzoyl-2-methylpropionyl)-L-proline; $[\alpha]_D^{23°} +275 \pm 1$(c, 0.956 ethanol). The fractions from the column which show a mixture of diastereomers by thin layer chromatography are rechromatographed. The later fractions showing one component are combined to give 4.1 g. of [S-(R*,R*)]-1-(3-acetylthio-3-benzoyl-2-methylpropionyl-L-proline as a white glass, $[\alpha]_D^{23°} -91° \pm 1$(c,1.08 ethanol).

EXAMPLE 70

[S-(R*,S*)]-1-[3-acetylthio-3-(3-fluorobenzoyl)-2-methylpropionyl]-L-proline and
[S-(R*,R*)]-1-[3-acetylthio-3-(3-fluorobenzoyl)-2-methylpropionyl]-L-proline As described in Example 55, 4.0 g. of (S)-1-[3-(3-fluorobenzoyl)-2-methylpropionyl]-L-proline (isomer A); m.p. 182°-185° C. is brominated to give the bromo derivative of isomer A [mixture of [S-(R*,S*)]-1-[3-bromo-3-(fluorobenzoyl)-2-methylpropionyl]-L-proline and [S-(R*,R*)]-1-[3-bromo-3-(3-fluorobenzoyl)-2-methylpropionyl]-L-proline]. Separation of the mixture by chromatography on a prep LC/500 column with hexane-ethyl acetate-acetic acid (75:25:2) as solvent gives 1.68 g. of pure diastereomer labelled X and 0.74 g. of pure diastereomer labelled Y. Reaction of diastereomer labelled X with potassium thioacetate in ethanol for 4 days gives the products of the Example (mixture of diastereomers). Reaction of diastereomer labelled Y with potassium thioacetate in ethanol for 4 days gives the products of the Example (mixture of diastereomers). Chromatography of the mixture on a silica gel column with ethyl acetate-hexane-acetic acid (5:5:0.2) separates the diastereomers to give [S-(R*,S*)]-1-[3-acetylthio-3-(3-fluorobenzoyl)-2-methylpropionyl]-L-proline, m.p. 158°-159° C.; $[\alpha]_D + 252° \pm 3$(c, 0.318 ethanol) and [S-(R*,R*)]-1-[3-acetylthio-3-(3-fluorobenzoyl)-2-methylpropionyl]-L-proline as a white glass, $[\alpha]_D - 147° \pm 1$(c, 0.834 ethanol).

EXAMPLE 71

[R-(R*,S*)]-1-[3-acetylthio-3-(3-fluorobenzoyl)-2-methylpropionyl]-L-proline and
[R-(R*,R*)]-1-[3-acetylthio-3-(3-fluorobenzoyl)-2-methylpropionyl]-L-proline As described in Example 55, (R)-1-[3-(3-fluorobenzoyl)-2-methylpropionyl]-L-proline (isomer B), m.p. 107°-108° C.) is separated from (S) diastereomer (isomer A). To the preceding compound (isomer B, m.p. 107°-108° C.) (4.76 g.) in 50 ml. of acetic acid is added 2.48 g. of bromine in 25 ml. of acetic acid. The mixture is stirred at room temperature for 18 hours. The mixture is filtered and the solid washed with pet ether (b.p. 30°-60° C.) to give 3.26 g. of white crystals, m.p. 128°-135° C. dec. From the mother liquors is obtained an additional 2.9 g. of solid. The solids are a mixture of [R-(R*,S*)]-1-[3-bromo-3-(3-fluorobenzoyl)-2-methylpropionyl]-L-proline and [R-(R*,R*)]-1-[3-bromo-3-(3-fluorobenzoyl)-2-methylpropionyl]-L-proline.

A sample (5.7 g.) of the mixture is reacted with sodium thioacetate [prepared from 1.8 ml. of thiolacetic acid and 0.885 g. of NaH(60% dispersion in oil)] in 150 ml. of acetonitrile at room temperature for 5 minutes. To the mixture is added 15 ml. of acetic acid and the solvent is removed under vacuum. The residue is partitioned between dichloromethane and water, the organic layer separated, washed with water, brine and dried (MgSO₄). The solvent is removed to give 5.9 g. of a gum. The gum is chromatographed over silica gel with ethyl acetate-hexane-acetic acid (5:5:0.2) as solvent to give 1.5 g. of [R-(R*,R*)]-1-[3-acetylthio-3-(3-fluorobenzoyl)-2-methylpropionyl]-L-proline as a white glass; $[\alpha]_D - 18° \pm 1$(c, 1.075 ethanol) and 0.45 g. of [R-(R*,S*)]-1-[3-acetylthio-3-(3-fluorobenzoyl)-2-methylpropionyl]-L-proline as white crystals, m.p. 86°-98° C. Recrystallization from dichloromethane-pet ether (b.p. 30°-60° C.) gives white crystals, m.p. 91°-93° C., $[\alpha]_D - 325 \pm 2$(c, 0.649 ethanol).

EXAMPLE 72

[S-(R*,S*)]-1-[3-Acetylthio-3-(4-bromobenzoyl)-2-methylpropionyl]-L-proline and
[S-(R*,R*)]-1-[3-acetylthio-3-(4-bromobenzoyl)-2-methylpropionyl]-L-proline To a solution of 100 g. of 4-bromobenzaldehyde in 400 ml. of tetrahydrofuran is added 104 g. of p-toluenesulfonic acid monohydrate. To the solution is added dropwise a solution of 94.5 ml. of morpholine in 100 ml. of tetrahydrofuran. The mixture is refluxed one hour, cooled and a slurry of 35.2 g. of potassium cyanide in 27 ml. of water added. The mixture is refluxed for 18 hours, cooled and poured into 1 liter of 10% potassium carbonate. The mixture is extracted with dichloromethane and the extract washed with water, 10% sodium bisulfite, saline and dried (MgSO$_4$). The solvent is removed under vacuum and the residue triturated with hexane and filtered to give 136.2 g. of white crystals, m.p. 88°–90° C. To the preceding α-(4-bromophenyl)-4-morpholineacetoniteile (136.2 g.) in 800 ml. of tetrahydrofuran is added 25 ml. of 30% potassium hydroxide in ethanol. To the stirred mixture is added slowly 42.5 ml. of metacrylonitrile in 200 ml. of tetrahydrofuran (exotherm 17°–34° C.). The mixture is stirred at room temperature for 18 hours, filtered and the filtrate concentrated to 200 ml. Addition of 100 ml. of ether, chilling and filtering gives 113.7 g. of white crystals, m.p. 170°–175° C. A mixture of the preceding compound, 500 ml. of acetic acid and 58 ml. of water is refluxed for one hour and the solvent removed. The residue is dissolved in dichloromethane and washed with water, saline and dried (MgSO$_4$). The solvent is removed to give 83 g. of 2-methyl-3-(4-bromobenzoyl)propionitrile; m.p. 101°–103° C. A mixture of the preceding compound, (83 g.) 400 ml. of 6 N HCl is refluxed for 18 hours. The mixture is chilled in an ice bath and filtered. The solid is washed with water and dissolved in 400 ml. of dichloromethane. The dichloromethane is dried (MgSO$_4$) and concentrated on a steam bath while hexane is added. Chilling and filtering gives 72.0 g. of white crystals of 3-(4-bromobenzoyl)-2-methylpropionic acid, m.p. 124°–125° C.

The preceding compound, (72 g.) is converted to N-hydroxysuccinimide ester, m.p. 99°–104° C., as for Example 7 and the activated ester (94.6 g.) is coupled as for Example 9 with 44.9 g. of L-proline to give 70.7 g. of 1-[3-(4-bromobenzoyl)-2-methylpropionyl]-L-proline as a gum (mixture of diastereomers). The gum is dissolved in hot ethyl acetate (200 ml.) and hexane (250 ml.) added. Chilling gives 19.3 g. of solid which is recrystallized from ethyl acetate to give 10.3 g. of (S)-1-[3-(4-bromobenzoyl)-2-methylpropionyl]-L-proline, m.p. 165°–167° C. (isomer A). From the mother liquors additional isomer A is obtained and purified by chromatography on silica gel. From the column (R)-1-[3-(4-bromobenzoyl)-2-methylpropionyl]-L-proline (isomer B) is obtained. To a mixture of 10.2 g. of isomer A in 125 ml. of acetic acid is added 4.43 g. of bromine in 20 ml. of acetic acid. Anhydrous hydrogen bromide is added and the mixture stirred 3 hours. The mixture is concentrated to ⅓ volume and poured into ice and water. The mixture is extracted with dichloromethane and the extract washed with water, brine and dried (MgSO$_4$). The solvent is removed under vacuum to give 12.7 g. of a glass (mixture of diastereomers). A mixture of 10.5 g. of the preceding glass in 150 ml. of acetonitrile is added dropwise to a mixture of sodium thioacetate (prepared from 2.9 ml. of thiolacetic acid and 1.4 g. of NaH (60% oil dispersion) in 150 ml. of acetonitrile. The mixture is stirred at room temperature for 18 hours, 30 ml. of acetic acid is added and the solvent is removed under vacuum. The residue is partitioned between dichloromethane and water. The dichloromethane layer is separated, washed with water, saline and dried (MgSO$_4$). The solvent is removed and the residue chromatographed on a silica gel column with ethyl acetate-hexane-acetic acid (5:5:0.2) as solvent. The early fractions containing mainly one component are combined and chromatographed on silica gel to give 5.1 g. of solid. Crystallization from ethyl acetate-hexane gives 3.5 g. of [S-(R*,S*)]-1-[3-acetylthio-3-(4-bromobenzoyl)-2-methylpropionyl]-L-proline as white crystals, m.p. 136°–138° C.; [α]$_D$+211°+1(c, 0.971, ethanol). The latter fractions from the column chromatography containing one component by thin layer chromatography are combined to give 1.2 g. of [S-(R*,R*)]-1-[3-acetylthio-3-(4-bromobenzoyl)-2-methylpropionyl]-L-proline as a white gla-s; [α]$_D$−69±1(c, 0.983 ethanol).

EXAMPLE 73

1-[3-Acetylthio-3-(2-naphthoyl)-2-methylpropionyl]-L-proline

As for Example 48, 2-naphthaldehyde is converted to 3-(2-naphthoyl)-2-methylpropionic acid and coupled to L-proline. The 1-[3-(2-naphthoyl)-2-methylpropionyl]-L-proline is separated into isomers A and B. Isomer A, (S)-1-[3-(2-naphthoyl)-2-methylpropionyl]-L-proline is reacted with bromine in acetic acid and the product reacted with sodium thioacetate in acetonitrile as for Example 72 to give the product of the example as a glass (mixture of diastereomers).

EXAMPLE 74

1-[3-Benzoyl-2-methyl-3-(2-pyrimidinylthio)propionyl]-L-proline

A sample of (S)-1-(3-benzoyl-2-methylpropionyl)-L-proline is reacted with bromine in acetic acid to give 1,84 g. of 1-(3-bromo-3-benzoyl-2-methylpropionyl)-L-proline (mixture of diastereomers). A solution of the preceding compound in 20 ml. of acetonitrile is added to a mixture of the sodium salt of 2-thiopyrimidine (prepared from 0.20 g. of NaIH (60% oil dispersion) and 0.56 g. of 2-thiopyrimidine) in 30 ml. of acetonitrile. The mixture is stirred for 18 hours and 0.4 ml. of acetic acid added. The mixture is filtered and the filtrate concentrated under vacuum. The residue is dissolved in dichloromethane and washed with water, saline and dried (MgSO$_4$). the solvent is removed and the residue (2.0 g.) chromatographed on a column of silica gel with ethyl acetate-hexane-acetic acid (75:25:2) as solvent to give 0.32 g. of [S-(R*,S*)]-1-[3-benzoyl-2-methyl-3-(2-pyrimidinylthio)propionyl]-L-proline (after precipitation from ether-hexane) as white glass, [α]$_D$+233°±2(c, 0.489 ethanol) and [S-(R*,R*)]-1-[3-benzoyl-2-methyl-3-(2-pyrimidinylthio)propionyl]-L-proline as a glass.

EXAMPLE 75

1-[3-Acetylthio-3-benzoyl-2-(phenyl)propionyl]-L-proline

A 0.01 mole sample of 3-benzoyl-2-(phenyl)propionic acid is dissolved in tetrahydrofuran and 0.01 mole of N,N-carbonyldiimidazole added. After stirring 3 hours at room temperature, 0.01 mole of L-proline t-butyl ester is added. After 24 hours the solvent is removed and 1-[3-benzoyl-2-(phenyl)-propionyl]-L-proline t-butyl ester isolated. The preceding compound is reacted with trifluoroacetic acid to remove the t-butyl group. Separation of isomers A and B is carried out as described for Example 69. Reaction of the isomers with bromine is acetic acid and reaction of the 1-[3-bromo-3- benzoyl-2-(phenyl)propionyl]-L-proline isomers with sodium thioacetate in acetonitrile as for Example 69 gives the products of the example. The product from isomer A is separated by chromatography to give [S-(R*,R*)] and [S-(R*,S*)]-1-[3-acetylthio-3-benzoyl-2-(phenyl)propionyl]-L-proline.

EXAMPLE 76

1-[3-Benzoyl-2-(carboxymethylthio)propionyl]-L-proline

To a suspension of 0.90 g. of 1-(3-benzoylacryloyl)-L-proline (prepared as described in Example 8) in 30 ml. of carbontetrachloride is added 0.28 ml. of mercaptoacetic acid. An additional 30 ml. of carbontetrachloride is added and the mixture stirred 3 days. The solvent is removed under vacuum. Carbontetrachloride (30 ml.) and 0.78 ml. of mercaptoacetic acid is added and the mixture stirred for 3 days. The solvent is removed and the residue chromatographed on a silica gel column with dichloromethane-methanol-acetic acid (90:10:2) as solvent. Fractions showing one spot by thin layer chromatography are combined to give 1.3 g. of clear gum. Placing the gum under high vacuum over night gives the product of the example as a glass, $[\alpha]_D^{23°} -31°\pm2$(c, 0.534 ethanol).

EXAMPLE 77

1-[2-Acetylthio-3-(4-bromobenzoyl)crotonyl]-L-proline

To a slurry of 16.0 g. of p-bromopropiophenone and 8.0 g. of glyoxylic acid in 90 ml. of water is added (with cooling) a mixture of 20 g. of 50% sodium hydroxide in 280 ml. of ethanol-water (1:1). The mixture is allowed to stand at room temperature for 20 hours and then heated to the boiling point for 30 minutes. The mixture is diluted with 800 ml. of ice and water, stirred several minutes and filtered. The filtrate is acidified with 5 N HCl and filtered to give 12.5 g. of β-(4-bromobenzoyl)-crotonic acid as tan crystals, m.p. 137°-144° C. The preceding compound (5.0 g.) is coupled with L-proline with N,N-carbonyldiimidazole in tetrahydrofuran to give 1-[β-(4-bromobenzoyl)crotonyl]-L-proline. A mixture of the preceding compound with thiolacetic acid in acetonitrile gives the product of the example as a glass.

EXAMPLE 78

1-[2-Acetylthio-3-(4-acetamidobenzoyl)crotonyl]-L-proline

As for Example 8, 3-(4-acetamidobenzoyl)crotonic acid is coupled to L-proline to give 1-[3-(4-acetamidobenzoyl)crotonyl]-L-proline. Reaction of the preceding compound with thiolacetic acid in carbontetrachloride as for Example 8 gives the product of the example as a glass.

EXAMPLE 79

1-[2-Acetylthio-2-methyl-3-(benzoyl)propionyl]-L-proline

As for Example 8, 3-(benzoyl)-2-methylacrylic acid is coupled to L-proline to give 1-[3-benzoyl-2-methylacryloyl]-L-proline. The preceding compound is reacted with thiolacetic acid in carbontetrachloride to give the product of the example as a glass.

EXAMPLE 80

1-[2-Acetyl-3-(4-acetamidobenzoyl)-2-methylacryloyl]-L-proline

Substitution of 3-(4-acetamidobenzoyl)-2-methylacrylic acid for benzoylacrylic acid in Example 8 gives the product of the example as a glass.

EXAMPLE 81

1-[2-Acetyl-3-(benzoyl)-2-methylcrotonyl]-L-proline

Substitution of 3-(benzoyl)-2-methylcrotonic acid for benzoylacrylic acid in Example 8 gives the product of the example as a glass.

EXAMPLE 82

1-[2-Acetylthio-3-(4-chlorobenzoyl)-2-methylpropionyl]-L-proline

Substitution of 3-(4-chlorobenzoyl)-2-methylacrylic acid for benzoylacrylic acid in Example 8 gives the product of the example as a glass.

EXAMPLE 83

1-[3-Benzoyl-2-(carboxymethylthio)-2-methylpropionyl]-L-proline

As for Example 76, 1-(3-benzoyl-2-methylacryloyl)-L-proline is reacted with mercaptoacetic acid to give the product of the example as a glass.

EXAMPLE 84

1-[3-Acetylthio-4-(benzoyl)butyryl]-L-proline

To a mixture of 4-benzoylcrotonic acid (0.01 mole) in tetrahydrofuran is added 0.01 mole of N,N-carbonyldiimidazole. After stirring for 2 hours, 0.01 mole of L-proline is added. The mixture is stirred for 24 hours to give 1-(4-benzoylcrotonyl)-L-proline. The preceding compound is reacted with thiolacetic acid in carbontetrachloride for 24 hours to give the product of the example as a glass.

EXAMPLE 85

1-[3-Acetylthio-3-(4-chlorobenzoyl)-2-methylpropionyl]-L-proline

To a slurry of 14.3 g. of 3-(4-chlorobenzoyl)-2-methylpropionic acid and 7.26 g. of N-hydroxysuccinimide in 150 ml. of dioxane is added 13 g. of N,N-dicyclohexylcarbodiimide. After stirring over night the mixture is filtered and the solid washed with ether. The combined filtrate and washings are concentrated under vacuum to give 20.1 g. of an oil. The oil is added to a solution of 7.25 g. of L-proline and 10.58 g. of sodium bicarbonate in 200 ml. of 50% ethanol. The mixture is stirred over night and filtered through diatomaceous earth. The filtrate is acidified with concentrated hydrochloric acid and extracted with dichloromethane. The extract is washed with water, dried (MgSO₄) and the solvent removed under vacuum to give an amber gum. The gum is dissolved in ethyl acetate-hexane and the mixture allowed to stand for several days. Filtration gives 3.23 g. of crystals, m.p. 170°-179° C. Recrystallization from ethyl acetate-hexane gives 2.81 g. of (S)-1-[3-(4-chlorobenzoyl)-2-methylpropionyl]-L-proline as colorless needles, m.p. 177.5°-179.5° C. The preceding compound is dissolved in 50 ml. of acetic acid and 1.27 g. of bromine added. The mixture is stirred overnight and the mixture concentrated under vacuum and poured into ice and water. The mixture is extracted with dichloromethane and the extract washed with water and dried (MgSO₄). The solvent is removed to give 3.15 g. of a white glass.

To a solution of 0.454 g. of sodium methoxide in 40 ml. of methanol is added 0.684 g. of thiolacetic acid. To the solution is added 3.07 g. of the preceding glass and the mixture is stirred for 3 days. The mixture is poured into ice and water and extracted with dichloromethane. The extract is concentrated to give 2.85 g. of product (mixture of diastereomers) as a white glass.

EXAMPLE 86

1-[3-(4-tert-butylbenzoyl)propionyl]-L-proline

As for example 85, 14 g. of 3-(4-tert-butylbenzoyl)-propionic acid is reacted with 6.9 g. of N-hydroxysuccinimide in the presence of 12.36 g. of N,N-dicyclohexylcarbodiimide to give 15.5 g. of 3-(4-tert-butylbenzoyl)propionic acid, N-hydroxysuccinimide ester, m.p. 135°-138° C. The preceding compound is added to a solution of 8.05 g. of L-proline and 11.76 g. of sodium bicarbonate in 400 ml. of ethanol-water (1:1). The mixture is stirred overnight, filtered and the filtrate concentrated under vacuum. The mixture is acidified with concentrated hydrochloric acid and extracted with dichloromethane. The solvent is removed to give an amber gum which chromatographed on 150 g. of silica gel with hexane-ethyl acetate (1:1) containing 2% acetic acid as solvent. From the column is obtained 12.4 g. of glass. To a solution of 9.8 g. of the preceding glass in 150 ml. of acetic acid is added 4.8 g. of bromine. The mixture is stirred overnight, concentrated and poured into ice and water. The mixture is extracted with dichloromethane and the extract concentrated to give 12.1 g. of a glass. The preceding glass is added to a solution of 1.94 g. of sodium methoxide and 4.56 g. of thiolacetic acid in 50 ml. of ethanol. After stirring for 2 hours, 1 ml. of acetic acid is added and the mixture diluted with water. The mixture is extracted with dichloromethane, the extract washed with water, dried (MgSO₄) and the solvent removed to give 12 g. of product as a yellow glass.

EXAMPLE 87

1-[3-(5-Benzoyl-2-pyrimidinylthio)-3-(4-chlorobenzoyl)propionyl]-L-proline

To a solution of 0.54 g. of sodium methoxide in 50 ml. of methanol is added 2.16 g. of 5-benzoyl-2-mercaptopyrimidine. To the mixture is added 3.88 g. of 1-[3-bromo-3-(4-chlorobenzoyl)propionyl]-L-proline and a yellow solid separated. Saturated sodium bicarbonate is added (solid dissolves) and the mixture is stirred for 5 minutes. Acetic acid (1 ml.) is added and the mixture stirred overnight. The mixture is diluted with water and filtered. The solid is dissolved in dichloromethane and the solution washed with water and dried. The solvent is removed to give 3.83 g. of product as a yellow glass.

EXAMPLE 88

1-[3-acetylthio-3-(5-indanylcarbonyl)propionyl]-L-proline

As for Example 85, 21.8 g. of 3-(5-indanylcarbonyl)-propionic acid is reacted with 11.5 g. of N-hydroxysuccinimide and 20.6 g. of N,N-dicyclohexylcarbodiimide in dioxane to give 27.6 g. of N-hydroxysuccinimide ester as yellow crystals, m.p. 112°-117° C. The preceding compound is added to a solution of 12.25 g. of L-proline and 17.8 g. of sodium bicarbonate in 600 ml. of ethanol-water (1:1). The mixture is stirred overnight, filtered and the filtrate concentrated and acidified to pH 4 with concentrated hydrochloric acid. The mixture is extracted with dichloromethane and the extracted concentrated to give 24 g. of an oil. On standing crystals separated and ethyl acetate-ether is added. Filtration gives 15.5 g. of 1-[3-(5-indanylcarbonyl)propionyl]-L-proline as white crystals, m.p. 89°-91° C.

To a solution of 13.9 g. of the preceding compound in 200 ml. of acetic acid is added 7.06 g. of bromine. The mixture is stirred overnight and concentrated under vacuum to an oil. The oil is chromatographed on a silica gel column with hexane-ethyl acetate (1:1) containing 2% acetic acid as solvent to give 14.9 g. of pale yellow oil. The oil is added to a solution of 2.55 g. of sodium methoxide and 5.78 g. of thiolacetic acid in 75 ml. of methanol and the mixture stirred overnight. Work-up by acidification, dilution with water, extraction with dichloromethane gives 13 g. of product as a pale yellow glass.

EXAMPLE 89

1-[3-(4-Chlorobenzoyl)-3-[5-(2-thenoyl)-2-pyrimidinylthio]propionyl]-L-proline

To a solution of 2.52 g. of sodium bicarbonate in ethanol-water is added 2.22 g. of 5-(2-theonyl)-2-mercaptopyrimidine. To the mixture is aded 3.88 g. of 1-[3-bromo-3-(4-chlorobenzoyl)propionyl]-L-proline. After stirring 15 minutes, 1 ml. of acetic acid is added and the mixture is stirred overnight. The mixture is filtered and the filtrate concentrated and extracted with chloroform. The chloroform extract is washed with water, dried (MgSO₄) and concentrated to give a glass. Chromatography on silica gel gives 3.9 g. of product as a glass.

We claim:

1. A compound selected from the group consisting of those of the formulae:

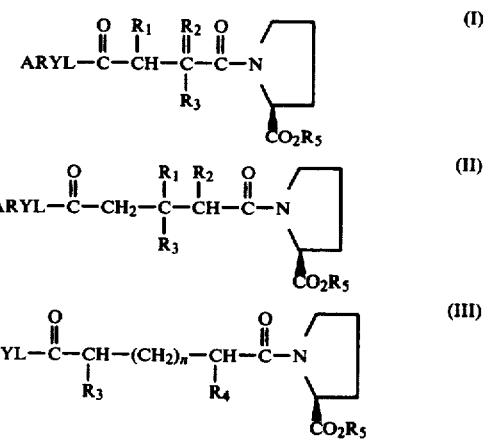

wherein n is zero or one; $R_1$ is hydrogen or alkyl having up to 3 carbon atoms; $R_2$ is hydrogen, phenyl or alkyl having up to 3 carbon atoms; $R_3$ is mercapto, formylthio, benzoylthio, alkanolythio having from 2 to 4 carbon atoms or moieties of the formulae:

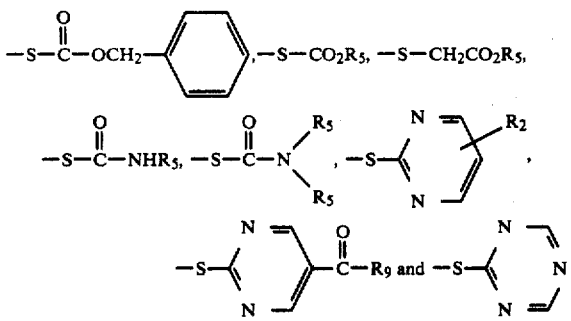

wherein R₉ is phenyl; R₄ is hydrogen, phenyl or alkyl having up to 4 carbon atoms; R₅ is hydrogen or alkyl having up to 4 carbon atoms; and ARYL is selected from the group consisting of 1-naphthyl, 2-naphthyl, 4-chloro-1-naphthyl, 5,6,7,8-tetrahydro-1-naphthyl, 5,6,7,8-tetrahydro-2-naphthyl, 4-methoxy-1-naphthyl, 5-acenaphthyl, 4-biphenylyl, 5-indanyl, 4-indanyl and moieties of the formula:

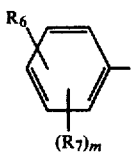

wherein R₆ is selected from the group consisting of hydrogen, fluoro, chloro, bromo, trifluoromethyl, cyano, amnio, phenoxy, halophenoxy, phenylthio, halophenylthio, p-cyclohexylphenoxy, alkyl having up to 4 carbon atoms, alkoxy having up to 4 carbon atoms, alkylamino having up to 4 carbon atoms, alkanoylamino having from 2 to 4 carbon atoms and alkoxycarbonyl having from 2 to 4 carbon atoms, R₇ is selected from the group consisting of chloro, fluoro, bromo, alkyl having up to 4 carbon atoms and alkoxy having up to 4 carbon atoms, and m is zero, one or two; and the pharmacologically acceptable cationic salts thereof when R₅ is hydrogen.

2. The compound according to claim 1, formula (I) thereof, wherein R₃ is acetylthio, ARYL is 1-naphthyl, and R₁, R₂ and R₅ are all hydrogen; 1[2-accrylthio-3-(1-naphthoyl)propionyl]-L-proline.

3. The compound according to claim 1, formula (I) thereof, wherein R₃ is benzoylthio, ARYL is 2-naphthyl, and R₁, R₂ and R₅ are all hydrogen; 1-[2-benzoylthio-3-(2-naphthoyl)propionyl]-L-proline.

4. The compound according to claim 1, formula (I) thereof, wherein R₃ is mercapto, ARYL is phenyl, and R₁, R₂ and R₅ are all hydrogen; 1-[2-mercapto-3-(benzoyl)pripionyl]-L-proline.

5. The compound according to claim 1, formula (III) thereof, wherein n is zero, ARYL is 4-biphenylyl, R₃ is acetylthio, and R₄ and R₅ are both hydrogen; 1-[3-acetylthio-3-(4-biphenylylcarbonyl)propionyl]-L-proline.

6. The compound according to claim 1, formula (II) thereof, wherein R₃ is acetylthio, ARYL is 4-chlorophenyl, R₁ is hydrogen, and R₂ is methyl; [S(R*,S*)]-1-[3-acetylthio-4-(4-chlorobenzoyl)-2-methylbutyryl]-L-proline.

7. The compound according to clai 1, formula (III) thereof, wherein n is zero, R₃ is acetylthio, ARYL is 4-chlorophenyl, R₄ is methyl and R₅ is hydrogen; 1-[3-acetylthio-3-(4-chlorobenzoyl)-2-methylpropionyl]-L-proline.

8. The compound according to claim 1, formula (III) thereof, wherein n is zero, R₃ is acetylthio, ARYL is 3-fluorophenyl, R₄ is methyl and R₅ is hydrogen; 1-[3-acetylthio-3-(3-fluorobenzoyl)-2-methylpropionyl]-L-proline.

9. The compound according to claim 1, formula (III) thereof, wherein n is zero, ARYL is 4-chloro-1-naphthyl, R₃ is acetylthio, and R₄ and R₅ are both hydrogen; 1-[3-acetylthio-3-(4-chloro-1-naphthoyl)propionyl]-L-proline.

10. The compound according to claim 1, formula (III) thereof, wherein n is zero, m is zero, R₆ is 4-(4-chlorophenoxy), R₃ is acetylthio, and R₄ and R₅ are both hydrogen; 1-{3-acetylthio-3-[4-(4-chlorophenoxy)benzoyl]propionyl}-L-proline.

11. The compound according to claim 1, formula (III) thereof, wherein n is zero, m is one, R₆ and R₇ are both chloro, R₃ is acetylthio, R₄ is methyl and R₅ is hydrogen; 1-[3-acetylthio-3-(3,4-dichlorobenzoyl)-2-methylpropionyl]-L-proline.

12. The compound according to claim 1, formula (III) thereof, wherein n is zero, m is one, R₆ is 4-methoxy, R₇ is 3-fluoro, R₃ is benzoylthio, and R₄ and R₅ are both hydrogen; 1-[3-benzoylthio-3-(3-fluoro-4-methoxybenzoyl)propionyl]-L-proline.

13. The compound according to claim 1, formula (III) thereof, wherein n is zero, m is two, R₆ is methoxy, R₇ is methoxy, R₃ is acetylthio, and R₄ and R₅ are both hydrogen; 1-[3-acetylthio-3-(3,4,5-trimethoxybenzoyl)propionyl]-L-proline.

14. The compound according to claim 1, formula (III) thereof, wherein n is zero, R₃ is acetylthio, ARYL is 3-trifluoromethylphenyl, R₄ is methyl, and R₅ is hydrogen; 1-[3-acetylthio-3-(3-trifluoromethylbenzoyl)-2-methylpropionyl]-L-proline.

15. The compound according to claim 1, formula (III) thereof, wherein n is zero, ARYL is phenyl, R₃ is acetylthio, R₄ is methyl and R₅ is hydrogen; [S-(R*,S*)-1-[3-(acetylthio)-3-(benzoyl)-2-methylpropionyl]-L-proline.

16. The compound according to claim 1, formula (III) thereof, wherein n is zero, ARYL is 3-fluorophenyl, R₃ is acetylthio, R₄ is methyl and R₅ is hydrogen; [S-(R*,S*)]-1-[3-acetylthio-3-(3-fluorobenzoyl)-2-methylpropionyl]-L-proline.

17. The compound according to claim 1, formula (III) thereof, wherein n is zero, ARYL is 4-bromophenyl, R₃ is acetylthio, R₄ is methyl and R₅ is hydrogen; [S-(R*,S*)]-1-[3-acetylthio-3-(4-bromobenzoyl)-2-methylpropionyl]-L-proline.

18. The compound according to claim 1, formula (III) thereof, wherein n is zero, ARYL is 4-bromophenyl, R₃ is acetylthio, R₄ is methyl and R₅ is hydrogen; [S-(R*,R*)]-1-[3-acetylthio-3-(4-bromobenzoyl)-2-methylpropionyl]-L-proline.

19. The compound according to claim 1, formula (III) thereof, wherein n is zero, ARYL is 4-chlorophenyl, R₃ is acetylthio, R₄ is methyl and R₅ is hydrogen; [S-(R*,S*)]-1-[3-acetylthio-3-(4-chlorobenzoyl)-2-methylpropionyl]-L-proline.

20. The compound according to claim 1, formula (III) thereof, wherein n is zero, ARYL is 4-chlorophenyl, R₃ is acetylthio, R₄ is methyl and R₅ is hydrogen; [S-(R*,R*)]-1-[3-acetylthio-3-(4-chlorobenzoyl)-2-methylpropionyl]-L-proline.

21. A compound according to claim 1, formula (III) thereof, wherein n is zero, ARYL is 2-naphthyl, R₃ is acetylthio, $R_4$ is methyl and $R_5$ is hydrogen; [S-(R*,S*)]-1-[3-acetylthio-3-(2-naphthoyl)-2-methylpropionyl]-L-proline.

22. A compound according to claim 1, formula (III) thereof, wherein n is zero, ARYL is phenyl, $R_3$ is acetylthio, $R_4$ is methyl and $R_5$ is hydrogen; [S-(R*,R*)]-1-[3-acetylthio-3-(benzoyl)-2-methylpropionyl]-L-proline.

23. A compound according to claim 1, formula (III) thereof, wherein n is zero, ARYL is 3-fluorophenyl, $R_3$ is acetylthio, $R_4$ is methyl and $R_5$ is hydrogen; [S-(R*,R*)]-1-[3-acetylthio-3-(3-fluorobenzoyl)-2-methylpropionyl]-L-proline.

24. A compound according to claim 1, formula (II) thereof, wherein ARYL is phenyl, $R_1$ is hydrogen, $R_2$ is methyl, $R_3$ is acetylthio and $R_5$ is hydrogen; [S-(R*,S*)]-1-[3-acetylthio-4-(benzoyl)-2-methylbutyryl]-L-proline.

25. A compound according to claim 1, formula (II) thereof, wherein ARYL is 3-fluorophenyl, $R_1$ is hydrogen, $R_2$ is methyl, $R_3$ is acetylthio and $R_5$ is hydrogen; [S-(R*,S*)]-1-[3-acetylthio-4-(3-fluorobenzoyl)-2-methylbutyryl]-L-proline.

26. A compound according to claim 1, formula (II) thereof, wherein ARYL is 2-naphthyl, $R_1$ is hydrogen, $R_2$ is methyl, $R_3$ is acetylthio and $R_5$ is hydrogen; [S-(R*,S*)]-1-[3-acetylthio-4-(2-naphthoyl)-2-methylbutyryl]-L-proline.

* * * * *